(12) United States Patent
Chen et al.

(10) Patent No.: US 9,366,601 B1
(45) Date of Patent: Jun. 14, 2016

(54) WAFER FABRICATION MONITORING/CONTROL SYSTEM AND METHOD

(75) Inventors: Jin-Jian Chen, Denton, TX (US); Oliver M. Chyan, Denton, TX (US)

(73) Assignee: University of North Texas, Denton, TX (US)

( * ) Notice: Subject to any disclaimer, the term of this patent is extended or adjusted under 35 U.S.C. 154(b) by 462 days.

(21) Appl. No.: 13/420,686

(22) Filed: Mar. 15, 2012

Related U.S. Application Data

(60) Provisional application No. 61/465,154, filed on Mar. 15, 2011.

(51) Int. Cl.
  *G01R 31/26* (2014.01)
  *H01L 21/66* (2006.01)
  *G01N 1/00* (2006.01)

(52) U.S. Cl.
  CPC ........................................ *G01N 1/00* (2013.01)

(58) Field of Classification Search
  USPC .......... 438/16, 278; 257/209; 250/559.4, 221, 250/231.13, 339.01, 339.07, 339.05, 250/339.06, 339.09, 339.12
  See application file for complete search history.

(56) References Cited

U.S. PATENT DOCUMENTS

| | | | |
|---|---|---|---|
| 3,487,223 A | | 12/1969 | St. John |
| 5,321,264 A | | 6/1994 | Kuwabara et al. |
| 5,381,234 A | | 1/1995 | Barbee et al. |
| 6,476,393 B1 | | 11/2002 | Yoshida et al. |
| 6,496,636 B1 * | 12/2002 | Braiman et al. ............. 385/129 |
| 7,520,956 B2 * | 4/2009 | Samukawa ............. H01L 22/34 156/345.13 |
| 8,320,728 B2 * | 11/2012 | Mizaikoff et al. ............. 385/131 |
| 2002/0125589 A1 * | 9/2002 | Katzir ............................. 264/1.23 |
| 2002/0173058 A1 * | 11/2002 | Liu et al. ......................... 438/16 |
| 2004/0056196 A1 * | 3/2004 | Yoshida et al. ............... 250/336.1 |
| 2010/0313875 A1 * | 12/2010 | Kennedy ......................... 126/652 |
| 2011/0090484 A1 * | 4/2011 | Osterlund et al. ................ 356/51 |
| 2013/0337585 A1 * | 12/2013 | Pfaff .................................. 438/16 |

OTHER PUBLICATIONS

Chyan, O. M. R., et al., "Trace Level Organics in Hydrofluroric Acid Determined by Attenuated Total Internal Reflection Infrared Spectroscopy," Anal. Chem., 1997, 69, pp. 2434-2437.
Ponnuswamy, T., et al., "Detection of Ni2+ by a Dimethylglyoxime Probe Using Attenuated Total-Reflection Infrared Spectroscopy," Anal. Sci., Apr. 2002, vol. 18, pp. 1-5.
Bhattacharyya, D., et al., "A New Class of Thin Film Hydrogels Produced by Plasma Polymerization," Chem. Mater., 2007, 19, pp. 2222-2228.
Rimal, S., et al., "Characterization of Post Etch Residues on Patterned Porous Low-k Dielectric Using Multiple Internal Reflection Infrared Spectroscopy," ECS Transactions, 2011, 41 (5) pp. 315-322.

* cited by examiner

*Primary Examiner* — Telly Green
*Assistant Examiner* — Damian A Hillman
(74) *Attorney, Agent, or Firm* — Talem IP Law, LLP

(57) ABSTRACT

A wafer fabrication monitoring/control system and method is disclosed. The invention utilizes Multiple Internal Reflection Infrared Detection (MIR-IR) to provide a highly sensitive (sub-10 nm, in-situ, ex-situ) on-wafer monitoring and characterization apparatus and method. The disclosed system and method has many practical applications to the development of advanced microfabrication technologies for sub-32 nm node CMOS semiconductor devices and provides support for formulation design, photolithographic patterning, etching/ashing of photoresists, plasma reactive ion etching (RIE) for trench/via patterning of low k dielectric, bottom anti-reflective coatings (BARCs), etch stop layers, and minimization/removal of plasma-etch polymers, development/confirmation of wet cleaning formulations and effectiveness for post CMP and post-etch cleaning.

12 Claims, 20 Drawing Sheets

WAFER FABRICATION MONITORING/CONTROL SYSTEM AND METHOD

CROSS-REFERENCE TO RELATED APPLICATION

This application claims the benefit of U.S. Provisional Patent Application No. 61/465,154, filed Mar. 15, 2011, which is hereby incorporated by reference in its entirety.

BACKGROUND

Semiconductor metrology is an important aspect in improving yield, reducing manufacturing costs, and shortening the product development cycle through its ability to monitor and detect defects at each stage of semiconductor processing. As features sizes become smaller and the materials used in semiconductor processing change, metrology solutions must also be able to accommodate these changes.

For example, low-k (k<3.9) and ultralow-k (ULK) (k<2.3) dielectrics have been introduced to reduce parasitic capacitance between metal interconnect layers. Unfortunately, ULK dielectrics have exhibited a sensitivity to etching and ashing processes, which can cause defects and decrease electrical reliability.

Once such dielectric is organo-silicate glass (OSG). To further decrease the dielectric constant (k) of OSG, the porosity of OSG may be varied through the replacement of Si—O with Si—C bonds by plasma-enhanced chemical vapor deposition (PECVD) to form carbon doped oxide (CDO). However, the increased carbon content from the carbon doping process can reduce the OSG's robustness and can increase the collateral plasma induced damage during reactive ion etch (RIE) photoresist stripping. In particular, oxygen plasmas will preferentially attack weaker Si—C bonds in ULK OSG and thus strip carbon, cause densification, and result in increased k values. In addition, carbon stripping by plasma processes makes low-k and ULK interlayer dielectrics (ILD) more prone to water damage during subsequent wet cleaning processes.

FIG. 1 illustrates polymer residue and damage to a ULK dielectric 101 after both an etching and post-etch cleaning process. As shown in FIG. 1, a mask layer 102 protects a top surface of the ULK dielectric 101 during the etching process to expose a lower Cu interconnect 103. However, as illustrated in FIG. 1, polymer residues may remain on sidewalls of the trench and/or via etched into the ULK dielectric, and the ULK dielectric 101 may have damage.

Consequently, the successful patterning of next-generation ULK/Cu interconnects through various non-damaging etching, ashing, and cleaning processes represents an increasingly challenging task to the semiconductor industry.

In addition to the challenge of handling weak porous ULK materials, a lack of sensitive (e.g., nanoscale level) metrology to guide systematic development of plasma etching, restoration, and cleaning processes has been an issue for semiconductor fabrication processes as feature sizes continue to shrink. Accordingly, there continues to be a need in the art for metrology with sub-10 nm sensitivity to guide next generation semiconductor process development and integration efforts.

BRIEF SUMMARY

Systems and methods for monitoring and testing patterning processes including etching, cleaning, and depositing of low k and ultra-low k dielectrics for semiconductor technologies are disclosed herein.

The present invention provides a highly sensitive (sub-10 nm, in-situ, ex-situ) on-wafer monitoring/controlling and characterization tool, Multiple Internal Reflection Infrared Detection (MIR-IR), that has many practical applications to the development of advanced microfabrication technologies for sub-32 nm node semiconductor devices. This includes but is not limited to a variety of wafer processes, including but not limited to formulation design, photolithography/patterning and etching/ashing of photoresist, plasma reactive ion etching (RIE) for trench/via patterning of low k dielectrics, bottom anti-reflective coatings (BARCs), etch stop layers and minimizing/removal of plasma-etch polymers, development/confirmation of wet cleaning formulation and effectiveness for post CMP and post-etch cleaning.

According to certain aspects of the invention, the information regarding changes in elemental composition, chemistry, bonding, and structure acquired by the MIR-IR techniques of various embodiments of the invention is used in assessing integrity of the dielectric, cross-linking densities of etch residues, and cleanability/removability of the residues from the dielectric.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

FIG. 3A shows an under-bevel wafer design and FIG. 3B shows a side-bevel wafer design.

FIG. 12A shows a representation of an external ATR IR spectroscopy method; FIG. 12B shows a representation of a MIR-IR system method in accordance with an embodiment of the invention; and FIG. 12C shows a comparison of a plot of the IR spectra obtained via the external ATR IR spectroscopy method and via the MIR-IR system method in accordance with an embodiment of the invention.

DETAILED DESCRIPTION

Figure 1:
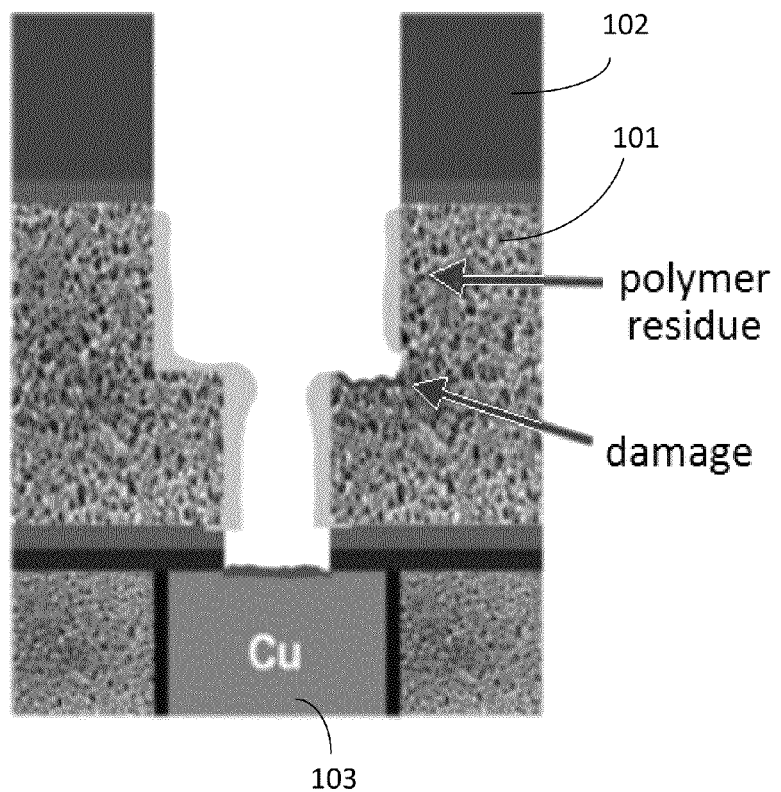
FIG. 1 illustrates polymer residue and damage to a ULK dielectric caused by an etching and post-etch cleaning process.

Infrared (IR) spectroscopy refers to the methods studying the interaction between matter and radiated energy in the IR spectrum. One common interaction studied via IR spectroscopy is a material's absorption in the IR spectrum radiation. For example, the IR spectrum of a sample can be recorded by passing a beam of IR light through the sample. When the frequency of the IR is the same as the vibrational frequency of a bond, absorption occurs. Examination of the transmitted light reveals how much energy was absorbed at each frequency (or wavelength). One common technique is to utilize Fourier transform IR (FT-IR) spectroscopy, where the information across an entire wavelength range is measured simultaneously and then transformed to provide a spectrum for the sample. The position, shape, and intensity of peaks in this spectrum indicate details about the molecular structure of the sample as well as the presence and, in many cases, the amount of a particular chemical substance in the sample.

IR generally refers to electromagnetic radiation emitting at wavelengths from about 750 nm (just beyond visible red light) to 1000 µm. The IR spectrum may be roughly classified into sub-regions including near-IR, mid-IR, and far-IR (named for their relation to the visible spectrum). The higher energy near-IR spectrum (generally defined as ranging from 0.75 µm to (1.4 µm-5 µm)) can excite overtone or harmonic vibrations. The mid-IR spectrum (generally defined as ranging from (1.4 µm-3 µm) to (25 µm-50 µm)) may be used to study the fundamental vibrations and associated rotational-vibrational structure. The far-IR spectrum (generally defined as ranging from (25 µm-50 µm) to 1000 µm), has low energy and may be used for rotational spectroscopy. The names and classifications of these sub-regions are conventions, and are only loosely based on the relative molecular or electromagnetic properties.

An IR source and detector of various embodiments of the invention may utilize any suitable frequency range within the IR spectrum. In certain embodiments, a mercury cadmium telluride (MCT) detector, which performs for IR wavelengths between 0.9 µm and 20 µm, is used.

Multiple Internal Reflection Infrared (MIR-IR) is an attenuated total reflectance (ATR) infrared sampling technique, which uses a property of total internal reflecting resulting in an evanescent wave. Systems and methods are provided herein for MIR-IR ex-site and in-situ measurements for semiconductor processing.

For some ATR techniques, a beam of IR light is passed through an external crystal substrate (crystal silicon, germanium, KRS-5 (Thallium Bromide-Iodide), zinc selenide, or diamond) in such a way that the beam reflects at least once off the internal surface of the external crystal substrate in contact with the sample being characterized to form evanescent waves extending into the sample on the substrate, the beam finally exiting the substrate for collection at a detector. A sample is placed on the external crystal substrate and often tightly held in place by face contact or narrow contact techniques.

The MIR-IR systems and methods of embodiments of the invention use a patterned wafer itself as the IR wave guide in place of the external crystal substrate receiving the IR beam. Since the patterned dielectric films of interested are deposited and formed directly on the wafer surface, a sample-contact problem occurring in other ATR techniques does not impede the sensitive detection of the subject invention. Embodiments of the systems and methods for MIR-IR are applicable to a wide variety of wafer types, including but not limited to, silicon wafers, germanium wafers, SiGe hybrid wafers, silicon-on-sapphire (SOS) wafers, GaAs wafers, epitaxial Si overlayer on Ge wafers, and/or other wafer variants/types utilized to fabricate electronic circuits and the like. Thus, the term "wafer" should be given its broadest possible meaning to encompass any wafer on which electronic circuits are patterned and through which an IR source/detector apparatus can be positioned to implement the teachings of the present invention system and/or method.

By using multiple reflections within an internal reflection element (e.g., the wafer), IR measuring sensitivity is enhanced and the signal-to-noise ratio is improved. The number of reflections may also be varied by varying the angle of incidence. The angle of incidence may be varied by adjusting one or more mirrors in an optical path of an IR beam incident the wafer on which structures being analyzed are formed. Alternatively, the incident surface of the wafer may be adjusted by changing the angle of a beveled edge. The penetration depth of the evanescent waves into the structure being analyzed depends on the wavelength of the light, the angle of incidence, and the indices of refraction for the wafer and the material(s) of the structure being analyzed.

In semiconductor device fabrication, photolithography allows intricate nanoscale patterns to be built on a silicon (or other material) wafer substrate using a photosensitive resist (generally referred to as "photoresist"), optical mask, and subsequent chemical treatments to develop/etch the photoresist. Photoresist often includes organic polymer blends with many functional groups that provide strong and distinct IR absorption peaks. According to one aspect of the invention, the chemical, structural, and bonding modifications occurring in photoresist can be characterized at process stages including, but not limited to, after spin coating, soft bake, photo-exposure, wet chemical developing, dry plasma etching/ashing, and wet resist stripping. In one embodiment, MIR-IR is used to assist in developing new photoresist formulations, as well as compositions and conditions for patterning and etching/ashing of the photoresist formulations. For example, light sensitivity, polymer composite composition, uniformity, and etching solubility can be tested using MIR-IR systems and methods of various embodiments of the invention.

The effects of chemical mechanical polishing processes (CMPs) with respect to underlying dielectric layers (pre-photoresist deposition or post photoresist removal) as well as wet etching process formulations can also be analyzed and improvements/optimizations developed.

Embodiments of the invention facilitate the development of practical and efficient plasma etching processes by enabling characterization and analysis of plasma-surface interactions on materials including low-k and ULK ILD, and bottom anti-reflective coatings (BARCs). Plasma etching, including reactive ion etching (RIE), performs many important microfabrication functions including the patterning of trench/via features on low-k or ULK ILD, the ashing/removal of photoresist, the etching/removal of BARCs, the minimizing/removal of plasma-etch polymers, the etching/removal of organic contaminations, and the restoration of damage to low-k or ULK ILD. However, lack of sensitive metrology to guide systematic development of plasma etching, restoration and cleaning processes continues to be a stumbling block for semiconductor fabrication processes in the next generation nodes.

For example, as semiconductor device foot prints continue to shrink, the post-etch residues left behind by plasma RIE processes, often buried in very deep trenches and side walls at the sub-32 nm node (and even more pronounced at the sub-22 nm node) interconnect microstructure, cause poor interlayer adhesion and increase electrical resistivity of Cu interconnect. These remaining post-etch residues can lead to high device defectivity and low production yield. Accordingly, MIR-IR systems and methods of embodiments of the invention can be used to guide the development of plasma etch processes that enable efficient post-etch cleaning (e.g., RIE formulations), sensitively detect trace post-etch residues in sidewalls of deep trench features, and guide subsequent post RIE cleaning processes.

In accordance with various embodiments of the invention, MIR-IR spectroscopy is used to monitor the decreasing IR absorbance ratio of cage to network Si—O—Si bonds of low-k and ULK ILD, which enables characterization of plasma-induced ILD damage. In addition to cage to network Si—O—Si bond analysis, the MIR-IR systems and methods of various embodiments of the invention can monitor $CH_3$ bending and Si—$CH_3$ rocking, as well as quantify etch polymer residues (including, but not limited to, —$CF_2$, —$CF_3$: —$SiF_3$, $SiF_2$, $SiF$).

The MIR-IR systems and methods of certain embodiments of the invention can achieve improved detection sensitivity and resolution over external ATR IR spectroscopy by taking advantage of the maximum evanescent wave interaction enabled by the intimate contact of sample and substrate (due to the substrate being the material on which the sample is formed). In contrast to external ATR IR spectroscopy, which lacks the feature size sensitivity to be useful in monitoring the progression of etching/cleaning processes (particularly where patterned structures include deep side-walls), certain embodiments of the invention show a sub 10 nm sensitivity. In addition, the ATR sample holders (using face contact and narrow contact techniques) that squeeze a sample tightly against ATR crystals in order to place the sample within the IR evanescent wave penetration depth (0.5-2 μm) for a meaningful sample detection may not be suitable for fragile samples, including porous ULK materials.

Figure 2:
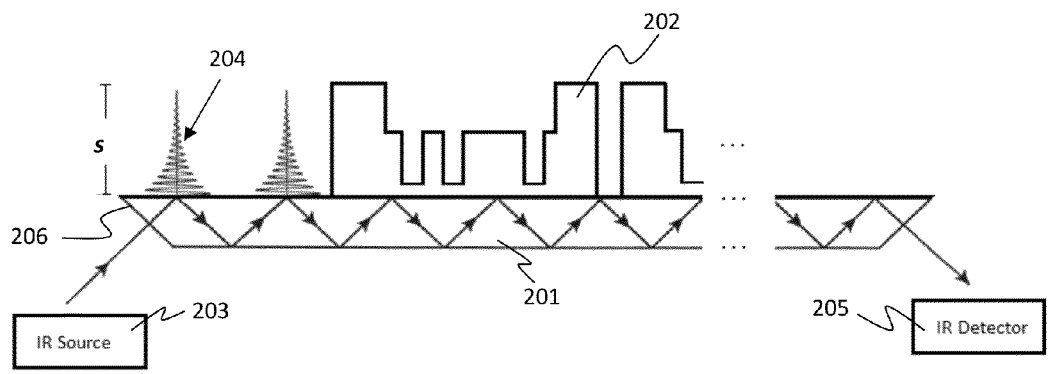
FIG. 2 shows a diagram illustrating multiple internal reflection infrared (MIR-IR) spectroscopy of a patterned dielectric layer in accordance with an embodiment of the invention.

FIG. 2 shows a diagram illustrating MIR-IR Spectroscopy of a patterned dielectric layer in accordance with an embodiment of the invention.

Referring to FIG. 2, a wafer 201 is provided having structures 202 patterned on the wafer 201. The structures 202 can include one or more dielectric layers and/or photoresist. Although the process stage for the structures 202 illustrated in FIG. 2 is a post-etching stage, the process stage for which structures provided on the wafer 201 can undergo the MIR-IR process include, but is not limited to, dielectric layer deposition, photoresist deposition (including pre- and post-exposure and development), dielectric layer etching, and photoresist removal (including stripping/ashing and residue removal).

During MIR-IR, the wafer 201 is irradiated with an IR source 203. In one embodiment, a single beam is directed to be incident an angled surface of the wafer 201. The beam from the IR source 203 is reflected within the wafer 201 and detected external to the wafer using an IR detector 205. By increasing the number of reflection points, the sampling "rate" (number or frequency of data points) increases. One method for increasing the sampling rate is to adjust the angle of incidence for the IR source 203 at an incident surface 206 of the wafer 201. Another method for providing additional data points is to perform multiple MIR-IR sampling. In one embodiment, multiple MIR-IR sampling can be performed by scanning a single IR beam along the width of the incident surface 206 or moving the wafer 201 such that the IR beam is incident the wafer 201 at particular intervals along the width of the incident surface 206. The movement of the wafer 201 can be carried out via, for example, a motorized stage driven by precision linear stepping motors. In another embodiment, multiple MIR-IR sampling can be performed by using multiple incident IR beams, each beam directed to a corresponding portion of the incident surface 206.

Radiation emitted from reflection points within the wafer 201 is emitted as evanescent waves 204 with a penetration depth s at the surface of the wafer 201. As shown in FIG. 2, an evanescent wave 204 has a maximum strength at the region right above the interface between the wafer 201 and a structure that may be formed on the wafer 201, and then decays exponentially away from the wafer surface. The evanescent waves 204 may be absorbed and/or reflected back within the wafer 201 to be detected by the IR detector 205 as the IR beam exits the wafer 201. The absorbance of the IR radiation into materials and/or structures 202 on the wafer 201 can be analyzed from the exiting IR beam, for example, to determine whether polymer residues and/or ILD damage is present and/or to characterize photoresists and etching processes. Although reflection points occur at both the front and back sides of the wafer, the loss/absorption occurring at the back side can be canceled as background when analyzing the detected signal.

The use of MIR-IR in this context permits detection of polymer residues and/or ILD damage during the structure 201 processing/fabrication since the absorption/reflection of the incident IR beam is impacted in minute ways by these polymer residues and/or ILD damage such that they may be tracked accurately during processing.

In many embodiments, to aid in the analysis of the absorbed/reflected evanescent waves, a computer system executing instructions retrieved from a computer readable medium is employed to analyze the data received from the IR detector. The computer system can include one or more computer processing units (CPUs), memory, mass storage (e.g., hard drive), and I/O devices (e.g., network interface, user input devices). A display can be provided to output graphic features and provide a graphical user interface (GUI). The one or more CPUs may include multiprocessors or multi-core processors. In certain embodiments, one or more digital signal processors (DSPs) may be included as part of the computer system in place of or in addition to a general purpose CPU. It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); or other media capable of storing computer-readable media now known or later developed. Computer-readable media should not be construed or interpreted to include any propagating signals.

Certain techniques set forth herein may be described in the general context of computer-executable instructions, such as program modules, executed by one or more computers or other devices. Certain embodiments of the invention contemplate the use of a computer system within which a set of instructions, when executed, can cause the system to perform any one or more of the methodologies discussed above. Generally, program modules include routines, programs, objects, components, and data structures that perform particular tasks or implement particular abstract data types.

In one embodiment, FT-IR spectra calculations are carried out (via the computer system) from the information (e.g., single channel spectra) obtained by the IR detector (via the read-out circuitry). For example, as performed using a FT-IR spectrometer, single channel spectra (total IR signal energy over a range of wavenumbers) are obtained from both the sample and the corresponding background. The FT-IR transmittance spectrum (percent transmittance % T vs. wavenumber) can then be calculated by dividing the sample spectrum by the background spectrum; and the absorbance spectrum (absorbance A vs. wavenumber) can be created by taking the $-\log$ of the % T transmittance spectrum. Once the absorbance spectrum is obtained and the sample characterized, the sample can be analyzed, for example, using quantitative analysis by specific IR peaks, quantitative analysis by scaled absorbance subtraction, or any other suitable methodology in accordance with embodiments of the invention.

For example, quantitative analysis by specific IR peaks (also referred to as a "single-component analysis") can be carried out when unique IR peaks, isolated from the background spectrum, can be identified in the absorbance spectrum. In particular, according to Beer's law $A = \in bC$, where A is the absorbance of a sample, $\in$ is the absorption coefficient, b is the path length, and C is the sample concentration, IR absorbance (A) is proportional to the sample concentration (C). Therefore, the IR absorbance of a specific functional group from a sample can be used to quantify the sample concentration. However, to obtain reliable absorbance spectrum for quantitative application, the background spectrum should be closely matched with the sample.

Scaled absorbance subtraction can be used in cases where a scaling reference (or common component) is available to isolate differences between the sample and the background.

For multiple MIR-IR sampling embodiments, the ensemble average of all MIR-IR spectra can be calculated. In certain embodiments, the multiple MIR-IR sampling improves IR detection sensitivity and spectra resolution.

In accordance with various embodiments of the invention, program modules (stored on a computer-readable medium) instructing a computer system to carry out one or more of the calculations and analyses described above are provided.

Figure 3A:
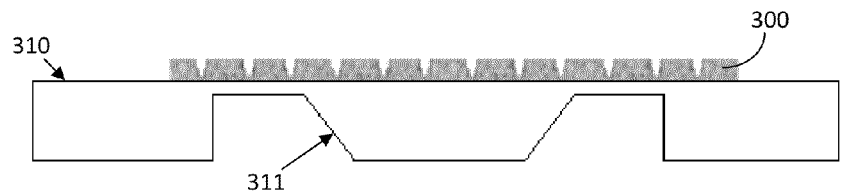
FIGS. 3A and 3B show wafer structures with a patterned film 300 in accordance with certain embodiments of the invention.
Figure 3B:
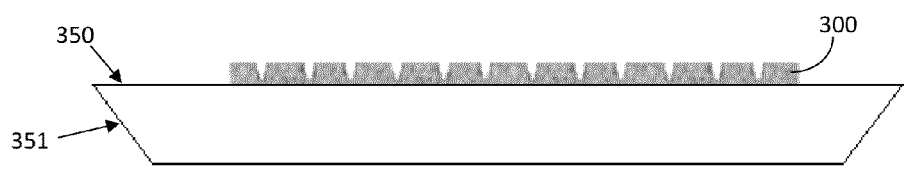

As described above, the patterned wafer is used as a waveguide for the MIR-IR system and methods of embodiments of the invention. An angled incident surface is provided to which the IR light is irradiated for passing through the waveguide of the wafer. In some embodiments, the angled incident surface is a beveled surface of the wafer, and the wafer can be etched or polished to form the beveled surface for the IR light (see 206 of FIG. 2). The forming of the beveled surface may be carried out before or after a deposition or etching process being performed on the wafer. FIGS. 3A and 3B show wafer structures with a patterned film 300 in accordance with certain embodiments of the invention. FIG. 3A shows an under-bevel wafer design 310 with beveled surfaces 311 formed from under the wafer. The beveled surfaces 311 can be fabricated by anisotropic etches (such as dry RIE and/or wet crystallogical etches) commonly used by microelectromechanical system (MEMS) device fabrication. FIG. 3B shows a side-bevel wafer design 350 with beveled surfaces 351 formed at sides of the wafer.

One or both of the designs shown in FIGS. 3A and 3B can be used for test wafers that are particularly fabricated for photoresist, plasma etch, and post-etch cleaning formulation and development. Test wafers do not require additional waveguide preparation and can be directly used in real-time MIR-IR monitoring. In certain embodiments, test wafers may be reusable. In one embodiment, the test wafers are reused after stripping and cleaning, which can save cost.

Figure 4:
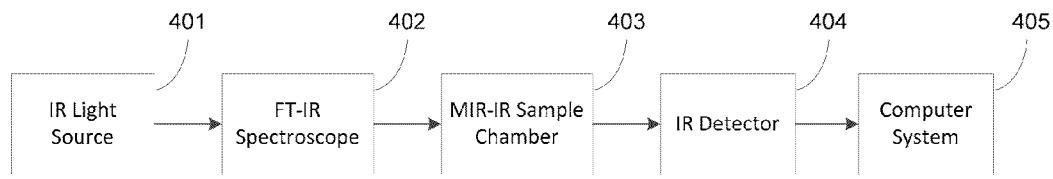
FIG. 4 shows a block diagram of a MIR-IR system in accordance with an embodiment of the invention.

FIG. 4 shows a block diagram of a MIR-IR system in accordance with an embodiment of the invention. Referring to FIG. 4, an MIR-IR system can include an IR light source 401, FT-IR spectroscope 402 (providing interferometer and beam splitter, as well as movable mirror), MIR-IR sample chamber 403, and IR detector 404 (with read-out circuitry). A computer-readable medium can be provided with instructions for performing analyses of data from the IR detector 404. In a further embodiment, a computer system 405 is included for receiving the data from the IR detector and executing instructions stored on the computer readable medium. In addition, a same or different computer-readable medium can be provided with instructions automating and/or controlling the MIR-IR system (e.g., for control of sample and incident IR beam). In one embodiment, the computer system 405 can be separate from the MIR-IR system and implemented via a laptop or desktop computer in which output from the IR detector 404 can be received.

In an embodiment for ex-situ testing of a wafer, the sample chamber 403 includes an X-Y-Z motorized stage on which a wafer can be disposed. In an embodiment for in-situ testing of a wafer, the sample chamber 403 can be the chamber in which process steps are carried out (e.g., a process chamber). In one such embodiment, a wafer stage of the process chamber can include one or more channels by which MIR-IR optics may be disposed. In certain embodiments, the wafer stage can be configured to isolate the MIR-IR optics below a wafer placed upon the wafer stage from the processing portion of the chamber.

Figure 5A:
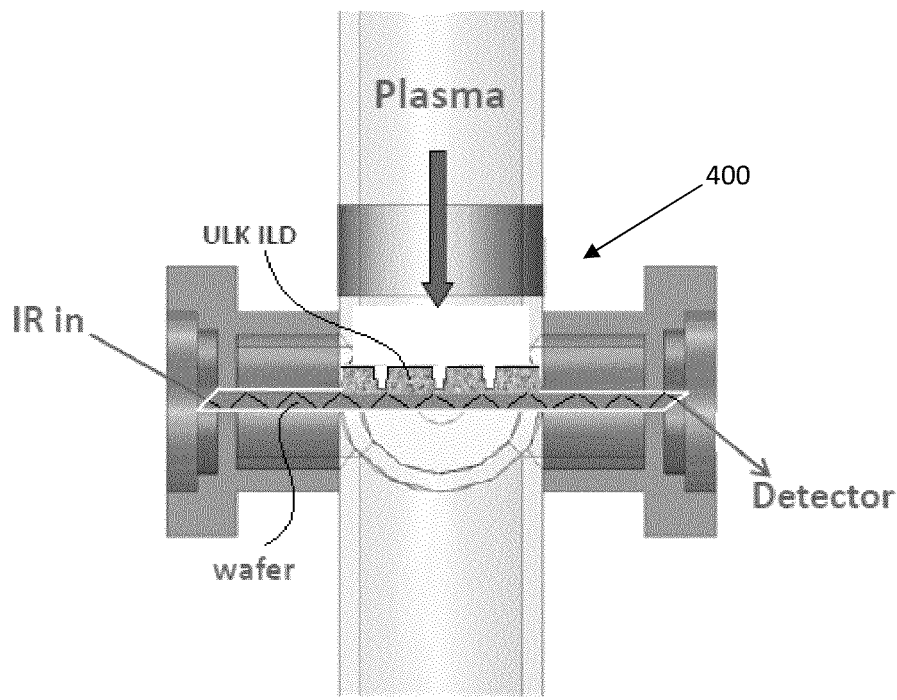
FIGS. 5A and 5B illustrate a system for in-situ testing of a wafer in accordance with one embodiment of the invention.
Figure 5B:
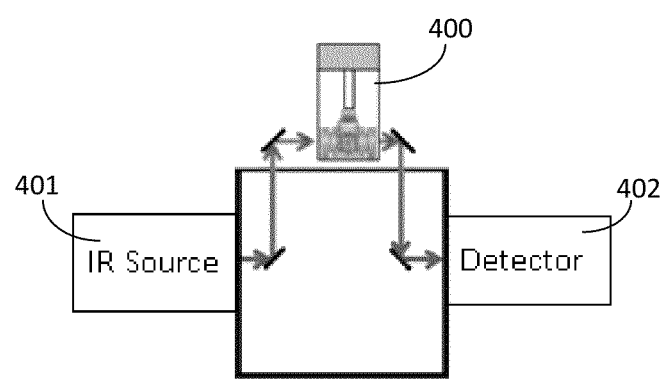

FIGS. 5A and 5B illustrate a system for in-situ testing of a wafer in accordance with one embodiment of the invention. For example, a process chamber 500 in which a wafer having an ILD layer being patterned (or cleaned) can be configured to receive an IR beam from an IR source 501 through an angled incident surface of the wafer and enable the exiting IR beam to be detected by a detector 502. The system illustrated in FIGS. 5A and 5B can be used for real-time measurements of thin films during plasma etching and/or post-etch cleaning.

It should be understood that while the side-beveled wafer design is illustrated in FIG. 5A, embodiments are not limited thereto. For example, test wafers having the under-bevel wafer design such as shown in FIG. 3A can be used in-situ. In addition, it should be understood that while certain embodiments are described with respect to a beveled incident surface for the wafer, the angled surface is not limited to being a beveled surface and other structures and techniques may be used to provide the angled surfaces. Further, the angled surfaces are not limited to the side-bevel and under-bevel designs.

In one implementation, the process chamber 500 can be part of a capacitively-coupled plasma RIE system in which a waveguide, prepared directly from a wafer on which ULK dielectric (and resist) is patterned, is disposed in the end caps with slit and proper seal machined into the RIE system. As described with respect to the systems and schemes of FIGS. 6-8 below, the real time characterization of patterned resist/ULK ILD samples under different RIE process conditions (including varying the chemistry, power, pulsed vs. continuous plasma, and bias) can be effectively investigated. MIR-IR analysis, combined with other characterization tools including, but not limited to, mass spectroscopy and UV-vis (ultra-violet-visible) spectroscopy, can be performed simultaneously in order to assess the effect of the plasma on the resist/ULK ILD film stack. Time dependent MIR-IR spectra collected in-situ provides insight into the effects of varying process conditions on the ULK-ILD structural integrity and polymer generation in real time and under vacuum conditions. The in-situ MIR-IR metrology of embodiments of the invention can be used to significantly shorten the development cycles of etching and cleaning processes for meeting critical dimension requirements and integration success.

Figure 6:
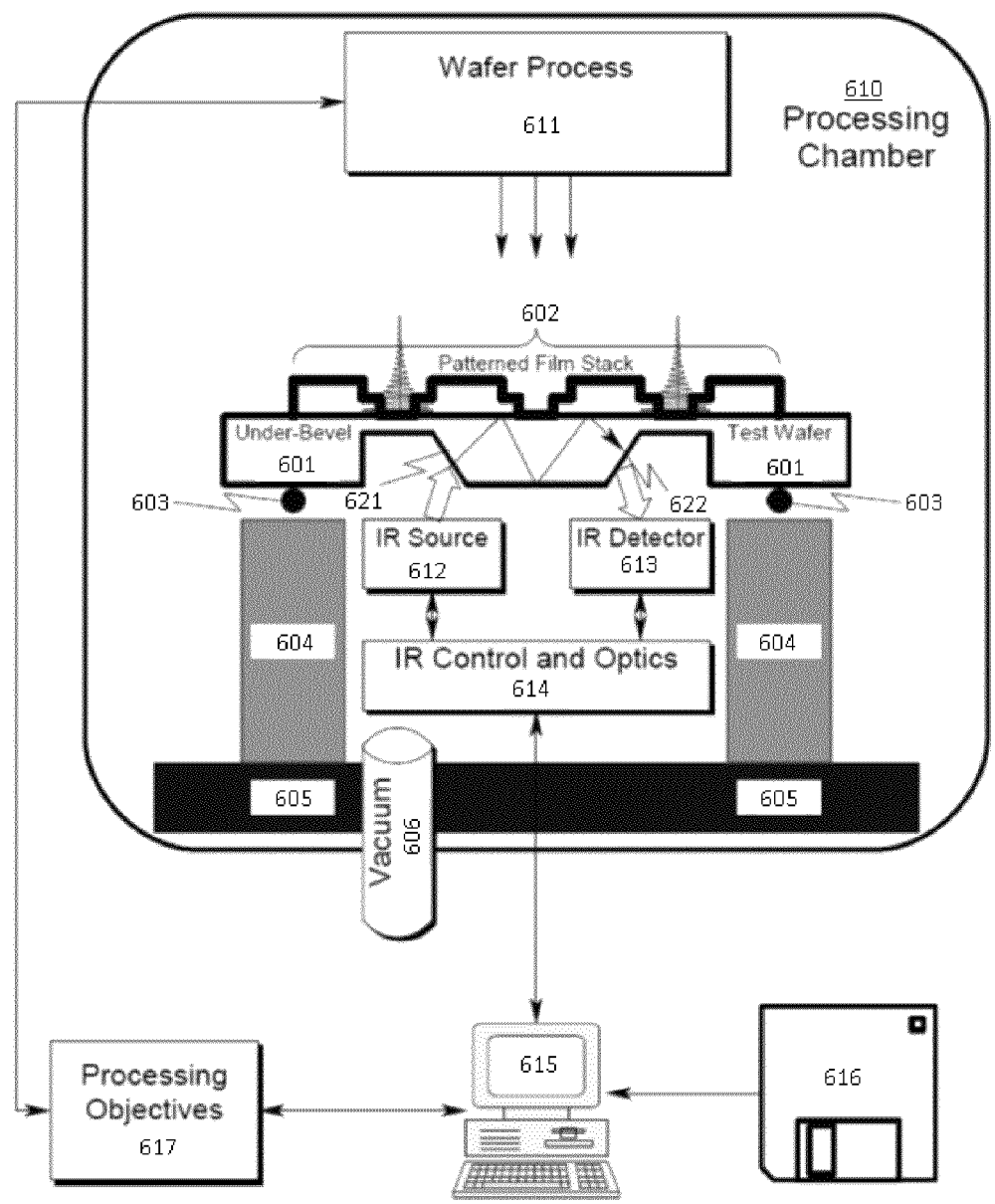
FIG. 6 illustrates a system for in-situ testing of a wafer in accordance with another embodiment of the invention.

For example, FIG. 6 illustrates a system for in-situ testing of a wafer in accordance with another embodiment of the invention. This system configuration generally incorporates a processing chamber 610 in which the under-bevel test wafer 601 with associated patterned film stack 602 is subjected to a wafer process 611 (for example, photolithographic patterning, etching/ashing of photoresists, RIE, post-etch cleaning, etc.) in a closed environment. The test wafer 601 of the embodiment shown in FIG. 6 contains paired beveled surfaces 621, 622 on its back face (the wafer face opposite the patterned film stack 602) that permit an IR source 612 and IR detector 613 to operate under control of an isolated/protected IR spectrometer and MIR-IR optics 614 system to irradiate the wafer 601 with the IR source 612 and detect the transmitted/absorbed spectra via the IR detector 613.

The back face of the wafer 601 can be isolated from the external environment by creating a seal between the back face of the wafer 601 and a wafer stage (incorporating a vertical chamber stack 604 and platform 605). O-rings 603 can be provided for improved sealing between the back face of the wafer and the vertical isolation chamber stack 604 and associated platform 605. A vacuum 606 may be utilized to evacuate the isolation chamber as needed to improve the detection/processing of MIR-IR signals from the angled back face of the wafer 601.

A computer system 615 may be integrated into communication with the IR spectrometer and MIR-IR optics control system 614 operated according to computer instructions stored on a computer-readable medium 616. These computer instructions can work in conjunction with processing objectives 617 to provide feedback to the wafer process 611 to provide real-time control of the wafer fabrication process.

In operation, the IR source 612 irradiates the first beveled edge 621 of the wafer 601. IR radiation is transmitted through the first beveled edge 621 of the wafer and beneath the patterned surface 602 structure on the wafer 601. In particular, the transmitted IR radiation evanescently probes the status of the patterned surface structure 602, resulting in scattered IR radiation that exits the second beveled edge 622 of the wafer 601 to the IR detector 613. The IR detector 613 detects the scattered IR radiation and reports the detection to the computer system 615. The computer system 615 can communicate with the IR control and optics subsystem 614 to analyze the detected IR radiation to determine a state (and/or effect) of a wafer process 611 applied to the wafer 601. One skilled in the art will recognize that these system components may be augmented or rearranged without limiting the teachings of the present invention.

In certain embodiments, the beveled edges 621, 622 may be multiply paired across the back face of the wafer 601 to form a plurality of IR waveguides that may be probed to determine characteristics over a variety of specific areas of the wafer 601 during processing. This may permit adjustment of the wafer process 611 spatially over the various areas of the wafer 601 to ensure uniform processing over the entire wafer surface over a wide variety of process variations and wafer surface conditions.

Figure 7:
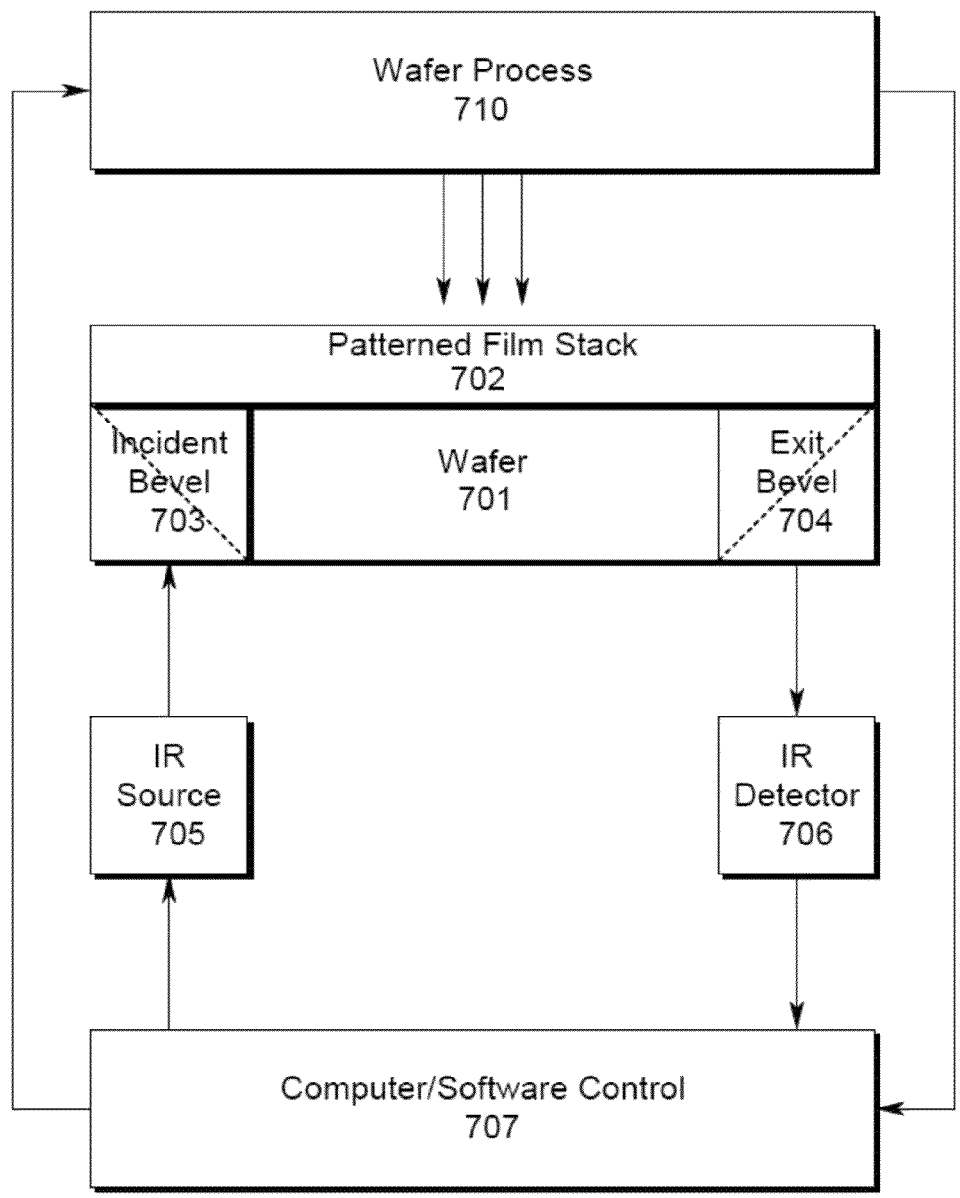
FIG. 7 shows an in-situ MIR-IR system for a side-bevel wafer configuration in accordance with certain embodiments of the invention.
Figure 8:
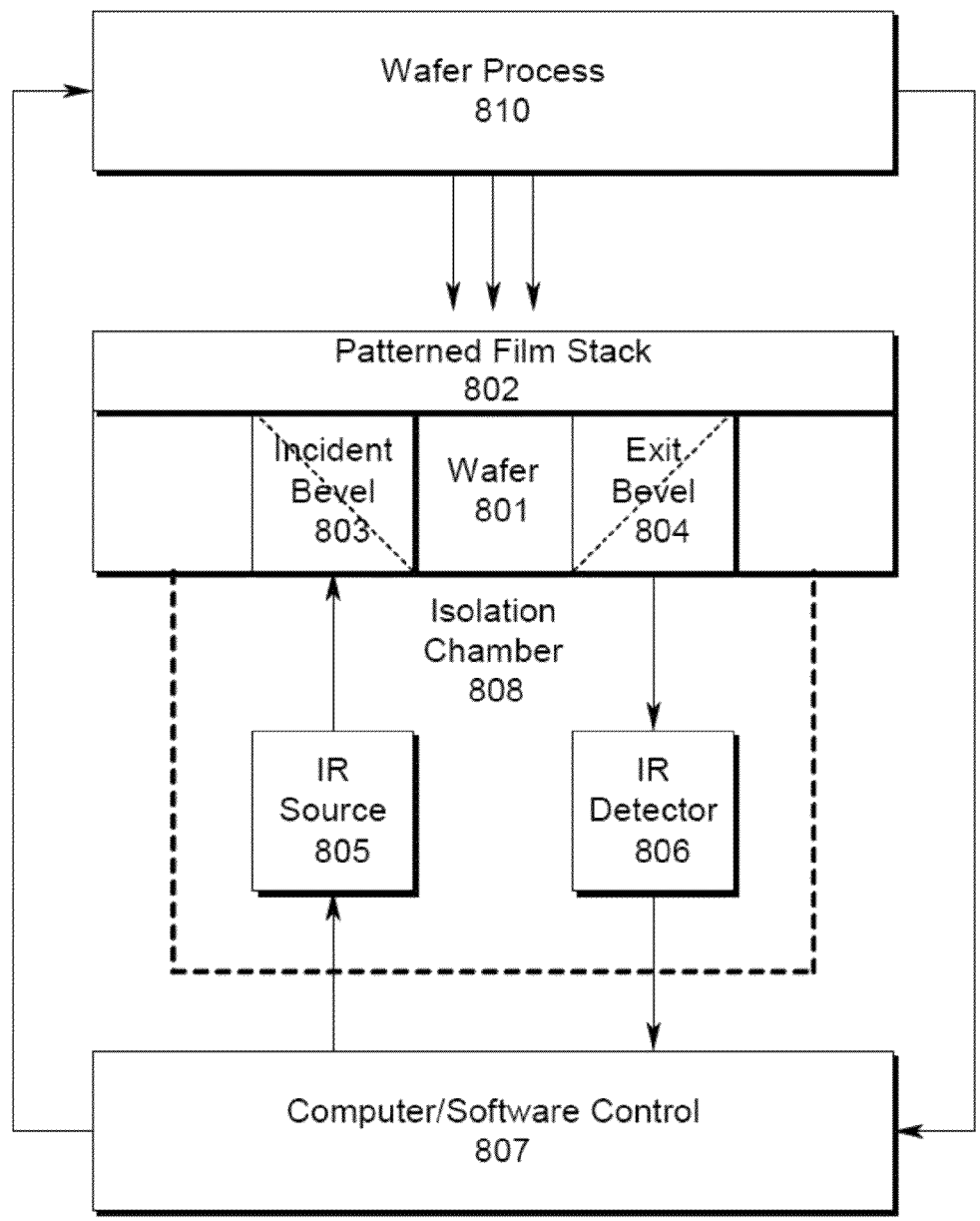
FIG. 8 shows an in-situ MIR-IR system for an under-bevel wafer configuration in accordance with certain embodiments of the invention.

FIGS. 7 and 8 show in-situ MIR-IR systems for side-bevel and under-bevel wafer configurations, respectively, in accordance with certain embodiments of the invention. Referring to FIG. 7, a system detecting the surface state of a wafer 701/patterned film stack 702 interface by the absorption/transmission of IR radiation through the wafer 701 is provided. For the MIR-IR system shown in FIG. 7, the wafer 701 is provided as an IR waveguide for sampling a patterned film stack 702 formed on the wafer 701. The waveguide structure is facilitated by incident 703 and exit 704 beveled surfaces at sides of the wafer 701 that permit transmission of IR signals from an IR source 705 through the incident beveled surface 703 and detection by an IR detector 706 as the IR radiation exits through the exit beveled surface 704. The absorption/transmission of IR radiation through the wafer 701 detected by the IR detector 706 is then analyzed by computer/software 707. The computer/software 707 can also control a wafer process 710 according to the analysis results.

An under-bevel wafer configuration is shown in FIG. 8. Similarly to the embodiments shown in FIG. 7, the surface state of a wafer 801/patterned film stack 802 can be determined interface by the absorption/transmission of IR radiation through the wafer 801. In the embodiment shown in FIG. 8, the wafer 801 forms a waveguide structure by incorporating incident 803 and exit 804 beveled surfaces beneath the wafer 801 back face to permit the entry of IR signals from an IR source 805 and detection of IR radiation from the exit beveled surface 804 by an IR detector 806. The absorption/transmission of IR radiation through the wafer 801 detected by the IR detector 806 is then analyzed by computer/software 807. The computer/software 807 can also control a wafer process 810 according to the analysis results. Differently from the system shown in FIG. 7, the system shown in FIG. 8 may utilize an isolation chamber 808 to protect the back face of the wafer 801 during the wafer process 810, and thus permits the system to be utilized in real-time while the wafer process 810 is utilized to fabricate the patterned film stack 802.

The wafer processing 810 monitored by the MIR-IR system can include, but is not limited to, on-wafer real time characterization and microfabrication process development of photolithography/patterning and etching/ashing of photoresist, plasma RIE for trench/via patterning of low k dielectric, bottom anti-reflective coatings (BARCs), etch stop layers and minimize/remove plasma-etch polymers, and develop/confirm wet cleaning formulation and effectiveness for post CMP and post-etch cleaning processes.

The isolation chamber 808 can minimize interferences of process contaminations at the bevel faces (803, 804) and back wafer surface by RIE plasma or wet chemical cleaning. In addition, by using an under-bevel design, the IR optics can be situated underneath the wafer.

In certain embodiments, the wafer remains stationary during the MIR-IR process and no optical re-alignment is performed.

The MIR-IR systems and methods of certain embodiments of the invention are used to identify specific functional groups of deposited thin films (for example, post-etch residues), and monitoring the thin films' corresponding cleaning evolution to optimize the post-etch cleaning chemistry formulation. The collected MIR-IR spectra enables the determination of functional groups as well as cross linking densities of polymer residues. By using the MIR-IR metrology of embodiments of the invention, insights can be obtained on the chemical and bonding modification across ULK ILD interfaces, trace post-etch residues can be quantified, and new effective post-etch cleaning processes can be developed with minimum ULK damage.

Both ex-situ and in-situ MIR-IR can be applied to characterize post-etch residues, develop new post-etch cleaning processes, and verify the cleaning effectiveness of a cleaning process step.

Figure 9:
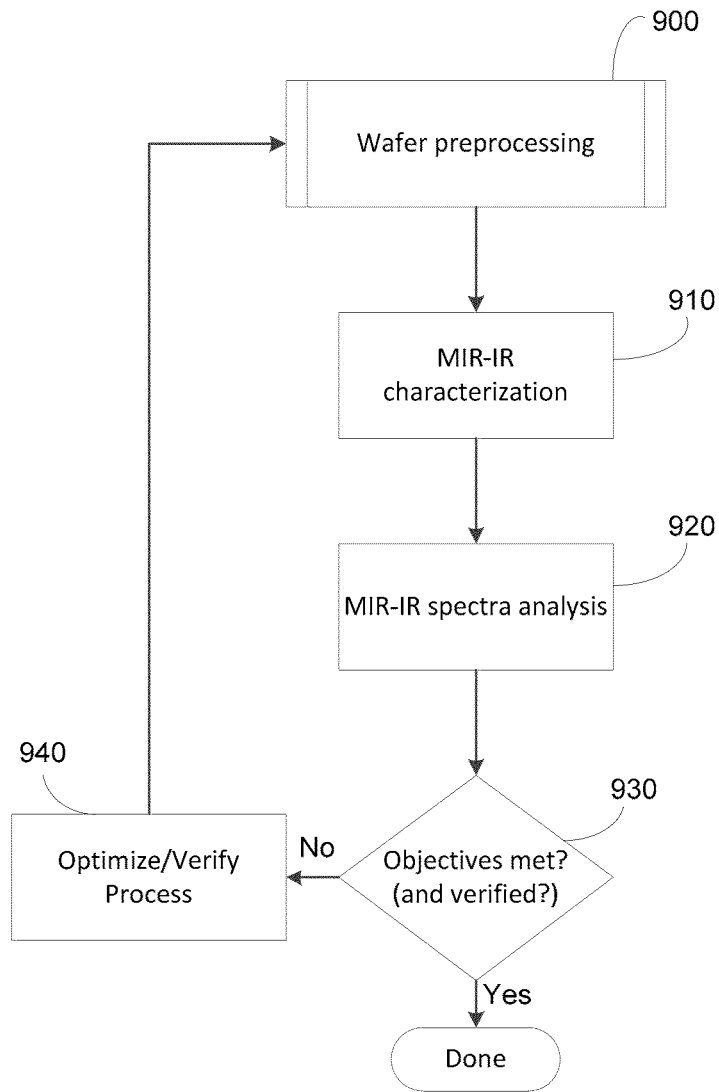
FIG. 9 illustrates a process for patterned wafer characterization and process development in accordance with an embodiment of the invention.

FIG. 9 illustrates a process for patterned wafer characterization and process development in accordance with an embodiment of the invention. Referring to FIG. 9, wafer preprocessing 900 can be performed. During wafer preprocessing 900, a processing step in a semiconductor fabrication process is performed and the wafer substrate is configured into an IR waveguide. The processing step may be performed before or after the forming the IR waveguide from the wafer. Where multiple processing steps are performed with respect to a particular wafer substrate, the forming of the IR waveguide from the wafer is performed once. In addition, the forming of the IR waveguide from the wafer does not need to be repeated if additional pre-processing steps are performed after performing MIR-IR characterization.

The processing step(s) carried out as part of a wafer preprocessing 900 can include, but is not limited to, spin coating of a photoresist directly on the wafer substrate or on a dielectric deposited on the wafer substrate, soft bake of the photoresist, photo-exposure of the photoresist, wet chemical developing of the photoresist, deposition of one or more dielectrics (e.g., a ULK dielectric, etch stop, etc.), etching of the dielectric, etching/removal of the photoresist, and post-etch polymer residue removal. In one embodiment where background reference spectra for a particular patterned wafer are not stored for use in the MIR-IR spectra analysis (step 920), the background reference spectra may be obtained via MIR-IR characterization and stored in a spectra database before performing the process step being analyzed and moving from the wafer preprocessing step 900 to the MIR-IR characterization step 910 of the process being analyzed. The background reference spectra obtained during the preprocessing may be stored in the spectra database and accessed during the MIR-IR spectra analysis.

Once wafer preprocessing is complete, the patterned wafer undergoes MIR-IR characterization 910 followed by MIR-IR spectra analysis 920. During MIR-IR spectra analysis, polymer residues or other materials being analyzed can be quantified using single-component analysis based on unique IR peak and/or scaled absorbance subtraction based on isolate reference peak. In one embodiment, the MIR-characterization obtained in step 910 may be compared to background reference spectra (for example, the background reference spectra can be used in performing a subtraction method). The background reference spectra can be stored in a spectra database accessed by a computer system during MIR-IR spectra analysis.

If the objectives for the processing step are met and verified (930), then the process is complete. However if the objectives for the processing step are not met (or have not yet been verified) (930), then the processing step(s) carried out as part of the wafer preprocessing 900 is adjusted for optimization (or a verification of the results is conducted) 940 before performing the processing step(s) in the preprocessing stage 900 again.

In accordance with certain embodiments of the invention, a silicon wafer on which a dielectric pattern is formed is used as the IR waveguide to enable multiple total internal reflections. For example, a 60 mm Si wafer providing an internal reflection element can achieve over 80 reflections. In addition, because of the inherent high refractive index of silicon (3.882 at 632.8 nm), the evanescent wave established at the interface between the Si wafer and a structure on the Si wafer has a useful penetration (i.e. sampling) depth s between 0.5-2 µm at mid-IR range. The sampling depth d of 0.5-2 µm is similar to the typical thickness of porous ultralow-k (ULK) interlayer dielectric (ILD) layers used in sub-32 nm node CMOS semiconductor devices.

According to another embodiment, a double-polished, undoped, or low dopant germanium wafer on which structures are fabricated can be used as the IR waveguide for the MIR-IR techniques. Si wafers tend to exhibit a decreased IR transmission (~30% T) from 1490 to 1176 cm$^{-1}$ (and less transmission at even lower wavenumbers) due to the combined effects of Si—Si phonon background absorption, native oxide absorption, and dopants absorption. The decreased IR transmission at these frequencies can make it difficult to measure ULK ILD materials that exhibit major IR absorption bands around 1300 to 750 cm$^{-1}$. However, low dopant Ge wafers can exhibit an even further sensitivity and spectra resolution for ULK dielectrics, as well as other materials such as SiCN and SiN (830-890 cm$^{-1}$), because of the ability of Ge wafers to maintain maximum IR transparency (~48% T) down to about 900 cm$^{-1}$ and near 40% T to about 600 cm$^{-1}$. In certain embodiments, using an epitaxial Si overlayer on Ge wafers can also achieve improved sensitivity.

Figure 10:
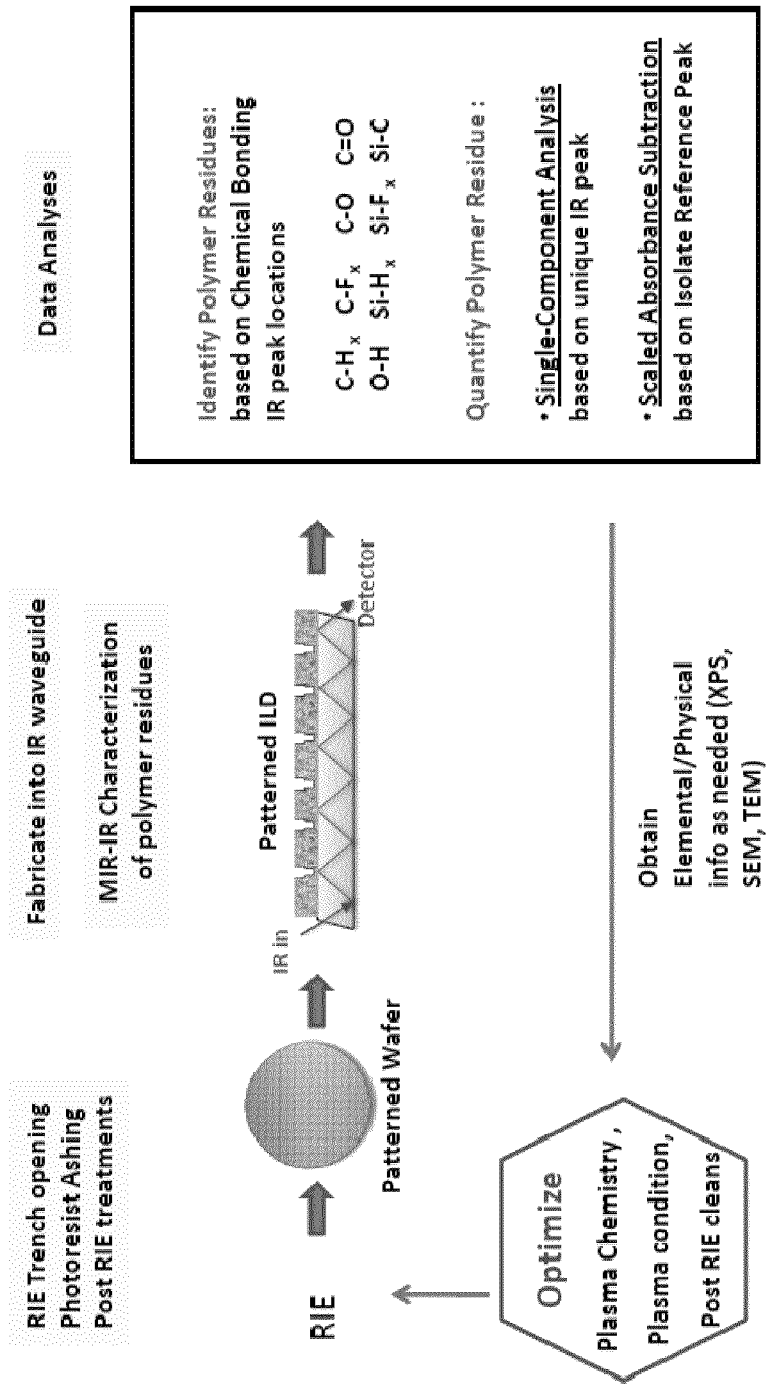
FIG. 10 illustrates a process flow for characterizing RIE etch and post-etch polymer residues in accordance with an embodiment of the invention.

FIG. 10 illustrates a process flow for characterizing RIE etch and post-etch polymer residues in accordance with an embodiment of the invention. For an ex-situ application, after fabricating the IR waveguides from a RIE processed patterned ULK wafer, the distribution of IR absorption intensities of $CF_2$, $CF_3$, $CH_2$, $CH_3$, $CF_xH_y$, and other functional groups may be identified from plasma generated polymer residues using MIR-IR. In certain embodiments, RIE trench opening, photoresist ashing, and post-etch treatments can be performed to provide the patterned ULK wafer. The MIR-IR characterization of the RIE etch and polymer residues can be carried out, and the results of the MIR-IR characterization (e.g., the absorbance spectrum) can then be analyzed to identify polymer residues based on chemical bonding IR peak locations. For example, C—$H_x$, C—$F_x$, C—O, C=O, C—N, O—H, $SiH_x$, $SiF_x$, and Si—C bonds can be identified. The polymer residue can then be quantified using single-component analysis based on unique IR peak and/or scaled absorbance subtraction based on isolate reference peak.

In a specific embodiment, a ULK film/stack can be deposited on a wafer that already has angled surfaces to provide the IR waveguide or is formed into an IR waveguide after deposition. MIR-IR can be performed to obtain baseline spectra of the ULK film/stack. Then, standard etches of the ULK film/stack using, for example, $CF_4$, $CH_2F_2$, CO, $H_2$, $N_2$, and Ar can be carried out. MIR-IR can be performed to obtain spectra of the etched film; and MIR-IR spectra analysis using the baseline spectra and the spectra obtained after the ULK film/stack etch allows determination of functional groups, as well as cross linking densities of polymer residues. For example, distribution of IR absorption intensities of $CF_2$, $CF_3$, $CH_2$, $CH_3$, $CF_xH_y$, and other functional groups can be identified from plasma generated polymer using MIR-IR.

In addition to the MIR-IR of embodiments of the invention, other metrology techniques may be carried out, including, but not limited to, x-ray photoelectron spectroscopy (XPS), scanning electron microscopy (SEM), and transmission electron microscopy (TEM), in order to obtain any further elemental or physical information from the sample. These additional characterization techniques may be performed in parallel or in a sequence in order to complement the MIR-IR analytical data. From the data collected, plasma chemistry, conditions, and post RIE cleans can be adjusted for optimization and applied to form patterned wafers. The MIR-IR characterization and optimization steps can be performed until processing objectives are met. For real-time monitoring, under-bevel test wafers may replace individual waveguides and the process optimization of RIE may be achieved in real-time.

Figure 11:
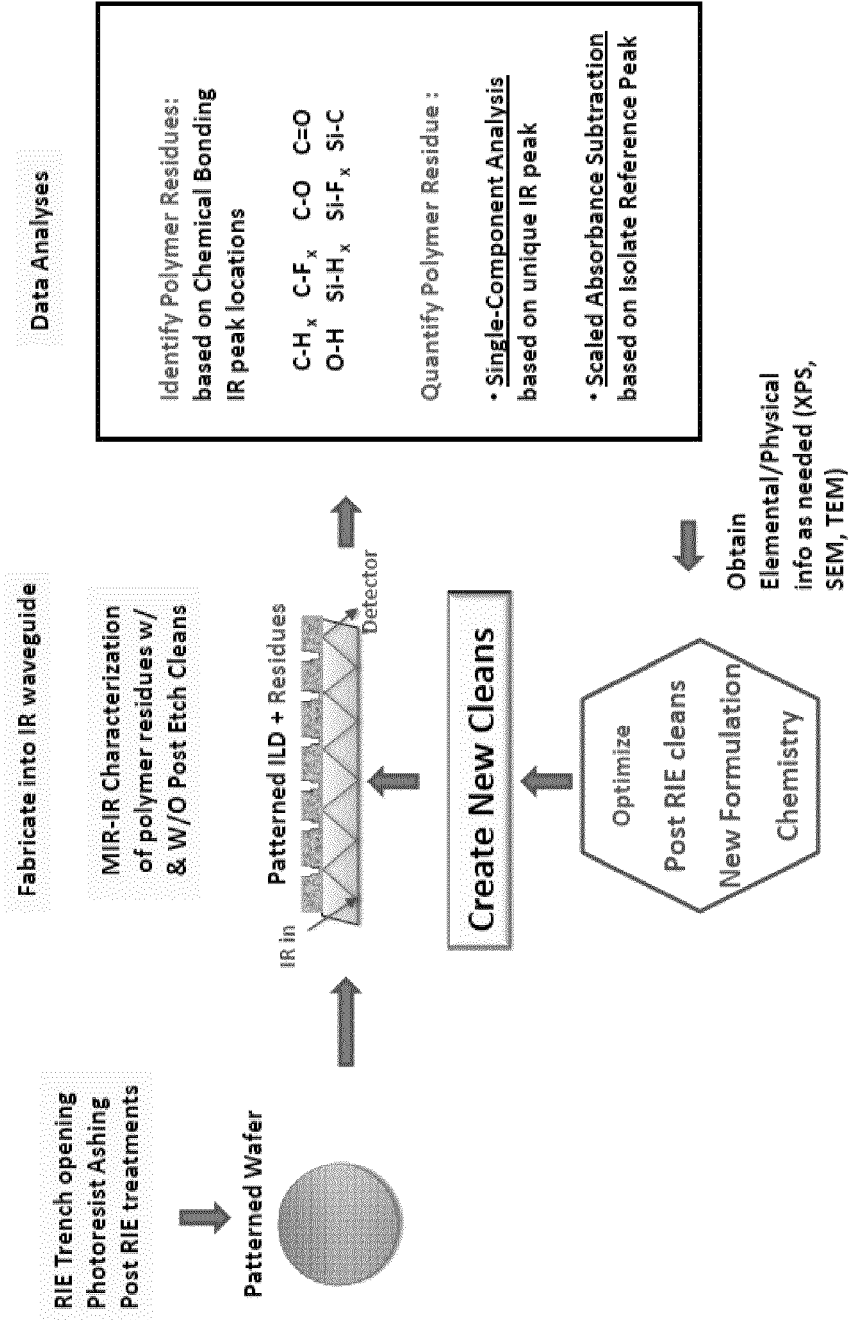
FIG. 11 illustrates a process flow for characterizing post-etch cleaning in accordance with an embodiment of the invention.

FIG. 11 illustrates a process flow for characterizing post-etch cleaning in accordance with an embodiment of the invention. Similarly to the optimization of RIE etch and post-etch polymer residue analysis, the post-etch cleaning processes can be optimized. For an ex-situ application, RIE trench opening, photoresist ashing and Post RIE treatments can be carried out to provide a patterned wafer. With the patterned wafer fabricated into an IR waveguide, MIR-IR characterization can be carried out for polymer residues with and without post-etch cleaning (e.g., before and after the post-etch cleaning) The results of the MIR-IR characterization (e.g., the absorbance spectrum) can then be analyzed. The distribution of IR absorption intensities of $CF_2$, $CF_3$, $CH_2$, $CH_3$, $CF_xH_y$, and other functional groups may be identified from plasma generated polymer residues using MIR-IR. In addition, polymer residues can be identified based on chemical bonding IR peak locations. For example, C—$H_x$, C—$F_x$, C—O, C=O, O—H, $SiH_x$, $SiF_x$, and Si—C bonds can be identified. The polymer residue can then be quantified using single-component analysis based on unique IR peak and/or scaled absorbance subtraction based on isolate reference peak. Other metrology techniques may also be carried out, including, but not limited to, XPS, SEM, and TEM, in order to obtain any further elemental or physical information from the sample. The combined data may be used to optimize the efficiency of post-etch cleaning processes and to develop new cleaning chemistries to achieve post-etch cleaning processing objectives. For real-time monitoring, under-bevel test wafers may replace individual waveguides and the process optimization of post-etch cleaning processes may be achieved in real-time.

It should be understood that many embodiments of the invention are described with respect to characterizing ULK dielectrics; however, embodiments are not limited to ULK dielectrics, and low-k and other films may be utilized as part of the patterned wafer being monitored.

A greater understanding of the present invention and of its many advantages may be had from the following examples, given by way of illustration. The following examples are illustrative of some of the methods, applications, embodiments and variants of the present invention. They are, of course, not to be considered in any way limitative of the invention. Numerous changes and modifications can be made with respect to the invention.

Example 1

Photolithography and Photoresist Characterization

Figure 12A:
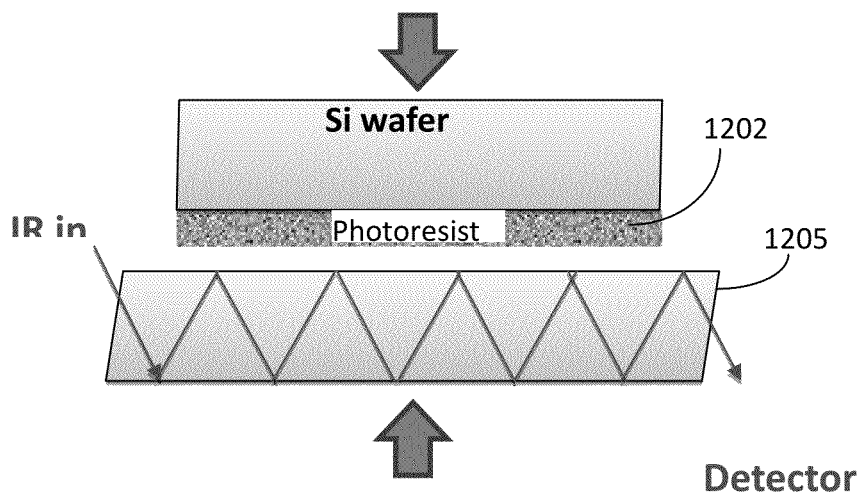
FIGS. 12A-12C provide a comparison between external ATR IR and MIR-IR capabilities for analyzing photolithography steps and characterizing photoresist.
Figure 12B:
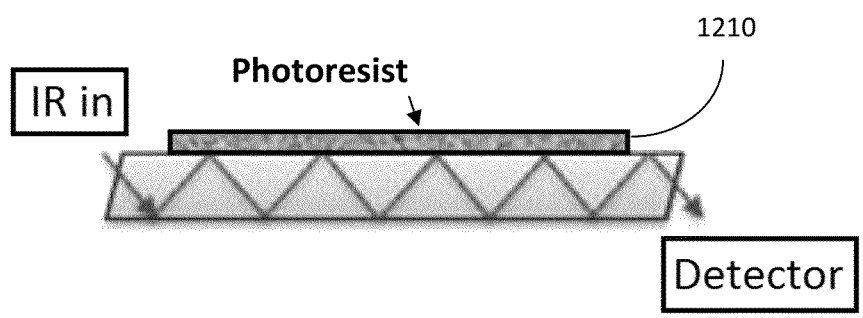
Figure 12C:
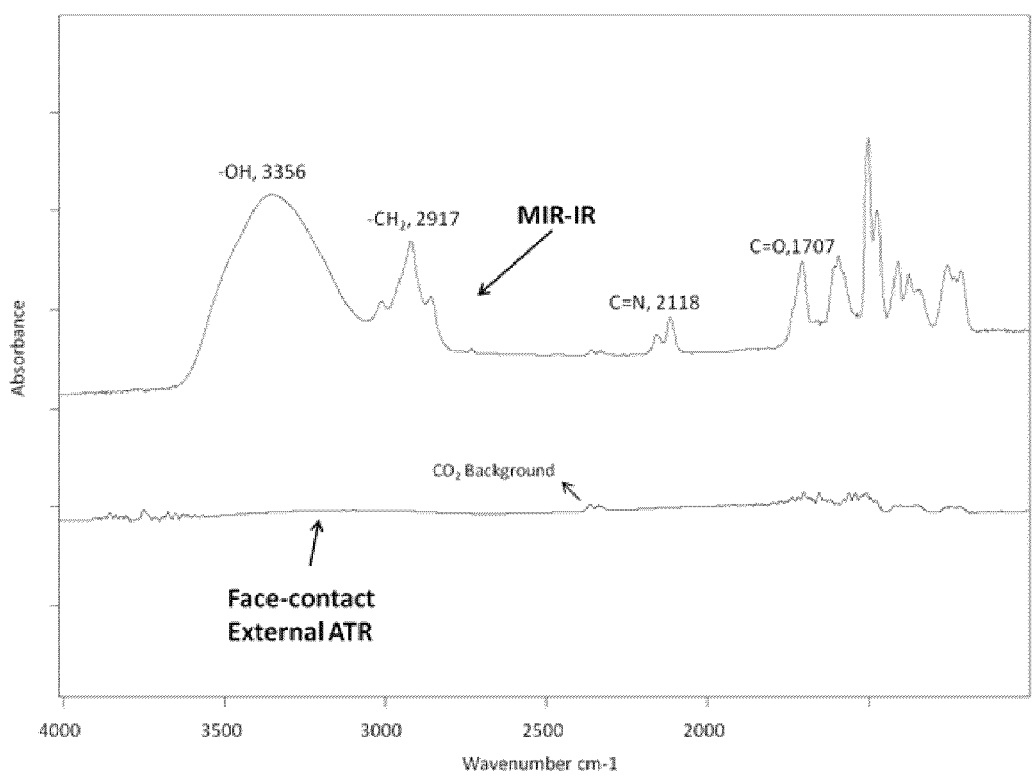

To illustrate the effectiveness of MIR-IR of certain embodiments of the invention for the characterization of photoresist, an experiment was carried out using a thin (<50 nm) photoresist coating on a Si wafer. FIGS. 12A-12C provide a comparison between external ATR IR and MIR-IR capabilities for analyzing photolithography steps and characterizing photoresist. FIG. 12A shows a representation of an external ATR IR spectroscopy method where a substrate having photoresist 1202 is pressed against a waveguide substrate 1205; FIG. 12B shows a representation of a MIR-IR system method where the substrate having photoresist 1210 provides a waveguide in accordance with an embodiment of the invention; and FIG. 12C shows a comparison plot of the IR spectra obtained via the external ATR IR spectroscopy method and via the MIR-IR system method in accordance with an embodiment of the invention.

As shown in the comparison plot of FIG. 12C, MIR-IR is capable of detecting the thin photoresist coating on a Si wafer with greater intensity and superior spectral resolution than is possible with external ATR IR. In addition, as illustrated by the sensitivity shown in the MIR-IR plot in FIG. 12C, MIR-IR is well suited for monitoring time-dependent chemical bonding and structure transformation of organic polymer subjected to plasma etching. For example, the C=N bonds (located at 2118 $cm^{-1}$ in FIG. 12C) from the photosensitive diazoquinone in this photoresist coating were found to break more easily, and hence were removed earlier under $O_2$ plasma ashing (which would be indicated by the loss of the peak as the etch progresses). Therefore, MIR-IR possesses a unique capacity of identifying specific functional groups of deposited thin films (sub 10 nm) and monitoring their corresponding reactivity evolution influenced by plasma process.

New insights obtained by MIR-IR on the chemical, structural and bonding modification on photoresist, after spin coating, soft bake, photo-exposure, wet chemical developing, dry plasma etching/ashing and wet resist stripping, can facilitate the development of new photolithography technology for the next generation semiconductor device.

Example 2

Plasma Reactive Ion Etching (RIE) Processes

To illustrate the effectiveness of an MIR-IR system and method of certain embodiments of the invention to characterizing RIE processes, experiments were conducted for removal of organic polymers (photoresist) deposited on 190 nm carbon doped oxide (CDO) thin film (an ILD material) on a silicon wafer.

Figure 13:
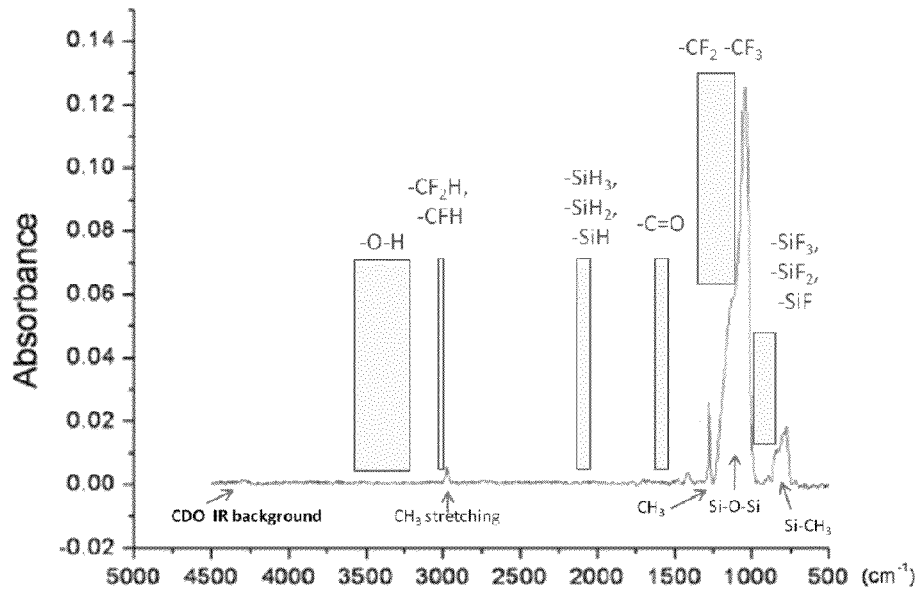
FIG. 13 shows a plot of specific IR peaks for RIE polymer characterization in accordance with an embodiment of the invention.

FIG. 13 indicates potential unique IR peaks from post-etch residues that can be used directly for quantification. With proper base-line determination, the absorbance (peak height) can provide the relative quantification of post-etch residues in the patterned ILD film stack.

As illustrated by the spectra plot of FIG. 13, the integrated IR peak absorbance enables a reliable basis for post-etch residues quantification. The results can be correlated to the H/F/O atomic ratio in etch gases, type of low-k/ULK ILD chemistry, and energetic characteristics of plasma. Concurrently, the IR absorbance of methyl termination (—$CH_3$, 2970 $cm^{-1}$) in a Si—O—Si cage provides a sensitive assessment of low-k/ULK ILD integrity before/after etches. The new chemical structural insights obtained by MIR-IR, combined with elemental and physical info (XPS, TOFSIMS, SEM, AFM), can provide valuable insight to guide plasma etch engineering design to achieve the desired etch profiles with good cleanability and minimal dielectric damage.

In addition (or as an alternative) to isolated IR peak analysis, scaled absorbance subtraction can be used to quantify post-etch residues.

Figure 14:
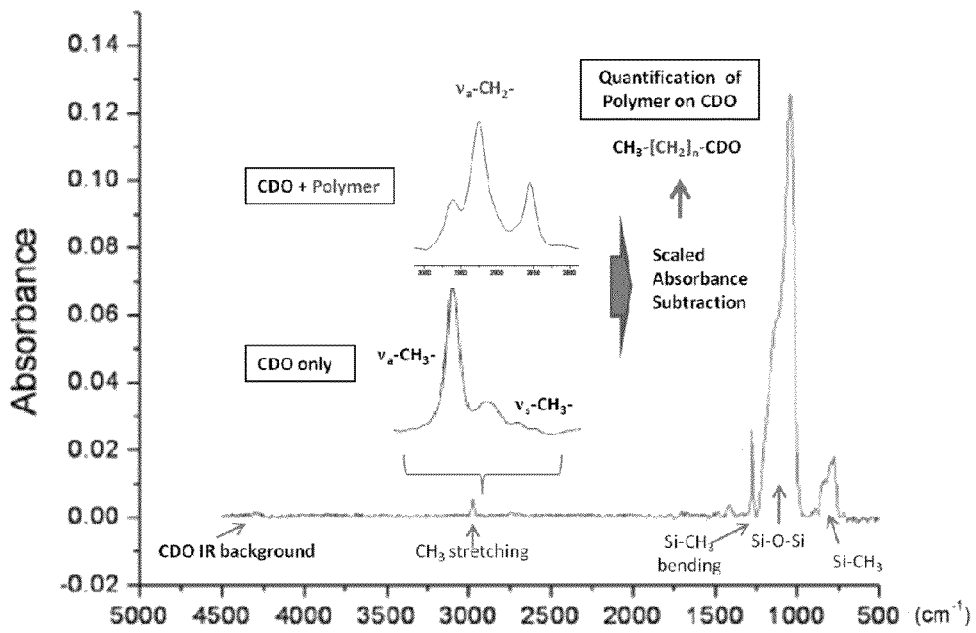
FIG. 14 shows plot illustrating polymer quantification by scaled absorbance subtraction in accordance with an embodiment of the invention.

FIG. 14 illustrates a scaled absorbance subtraction method that relies on the asymmetric —$CH_3$ stretching peak (2970 $cm^{-1}$), originated from —$CH_3$ groups unique to carbon doped low-k/ULK ILD, as the scaling reference to isolate the IR absorbance of post-etch residues from its ULK ILD background. As shown in the FIG. 14, the CDO film is mostly populated in its silicon oxide matrix with —$CH_3$ groups that give a strong and well-defined asymmetric —$CH_3$ stretching peak at 2970 $cm^{-1}$. Therefore, the IR absorbance peak at 2970 $cm^{-1}$ can be directly correlated with the quantity of ULK ILD film. In contrast, the post-etch residues (mainly organic polymers with fluorine substitutes) has a different IR absorption peak at 2925 $cm^{-1}$ cm that arises from asymmetric stretching of —$CH_2$ dominated in chemical structural framework of organic polymer.

Figure 17:
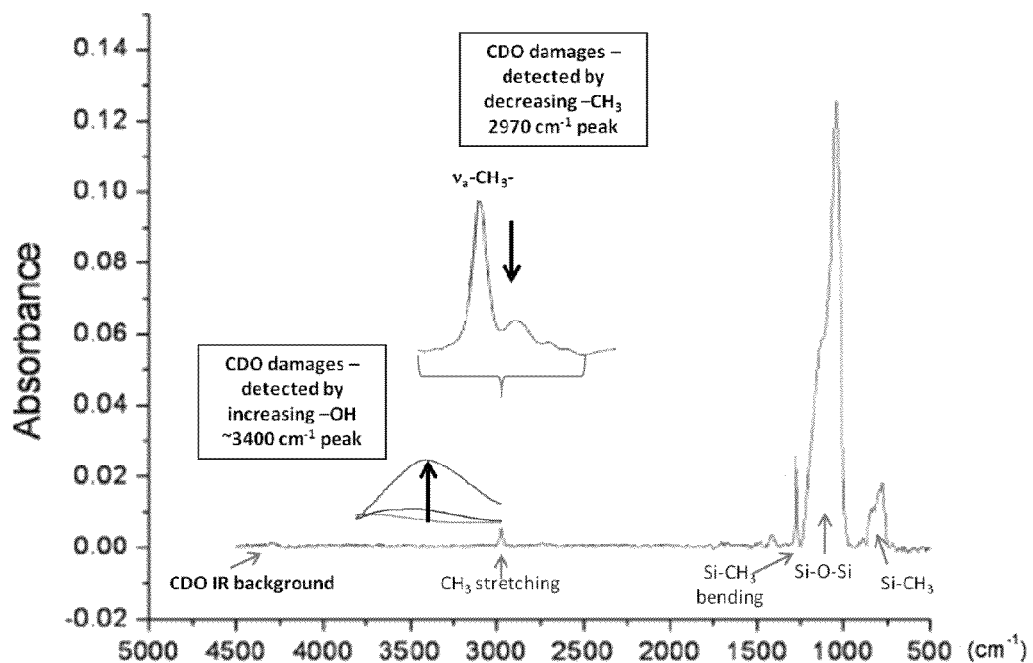
FIG. 17 shows plots for polymer quantification by scaled absorbance subtraction in accordance with an embodiment of the invention.

In the experiments, during the RIE etching for trench/via patterning on the CDO ILD film, the amount of CDO film is continuously decreased as the RIE etching progressed. Therefore, a CDO-only background keeps changing and, thus, would be assumed to prevent reliable scaled absorbance subtraction. However, by using the MIR-IR detection sensitivity and resolution, several specific IR peaks were able to be identified from the CDO ILD film to properly re-construct the best matched possible background for quantifying post-etch residues using the scaled absorbance subtraction method. As shown in FIGS. 14 and 17, for example, the asymmetric —$CH_3$ stretching peak at 2970 $cm^{-1}$ can be used as the reference peak to determine the remaining quantities of CDO ILD film after etch or cleaning. According to the extent of IR peak decreases observed in 2970 $cm^{-1}$, a proper CDO-only background can be proportionally calculated from the standard CDO only spectra, collected prior to the RIE etching or post-etching cleaning treatment.

Figure 15A:
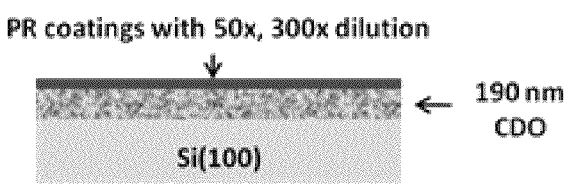
FIG. 15A shows a representational wafer structure for characterizing photoresist thin films on a CDO wafer according to an embodiment of the invention.
Figure 15B:
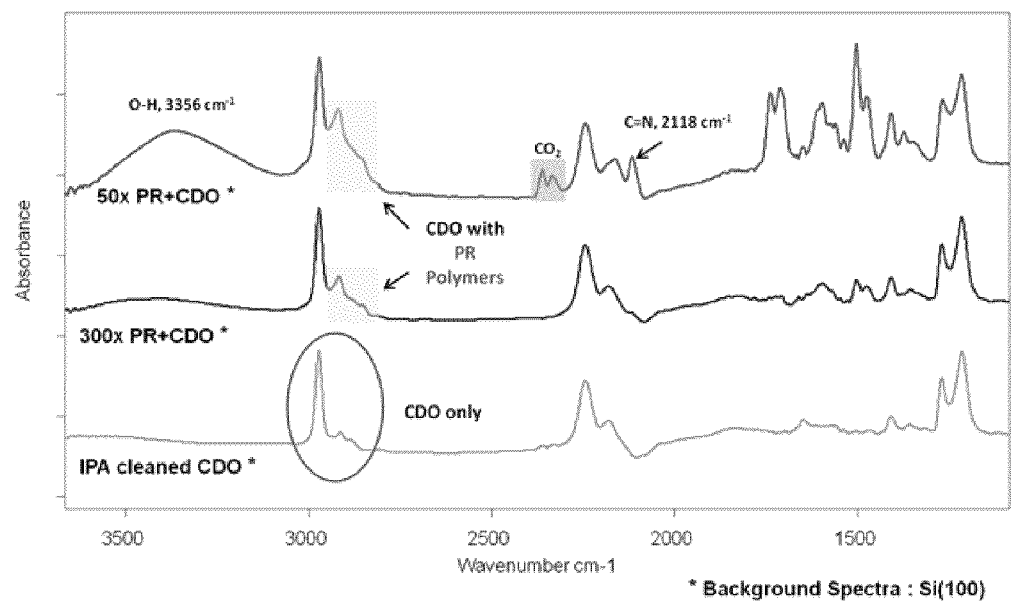
FIG. 15B shows plots of MIR-IR spectra of photoresist thin films on a CDO wafer in accordance with an embodiment of the invention.
Figure 16A:
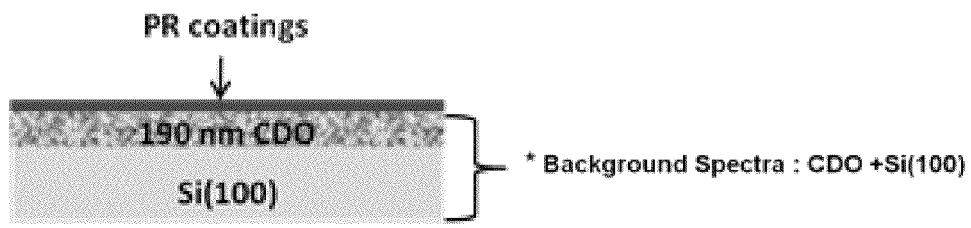
FIG. 16A shows a representational wafer structure for characterizing photoresist thin films on a CDO wafer according to an embodiment of the invention.
Figure 16B:
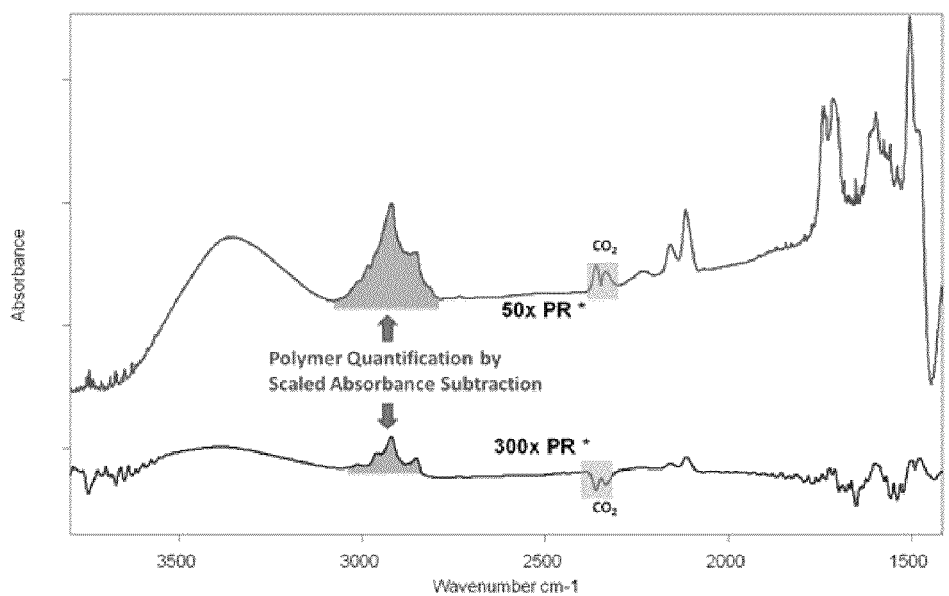
FIG. 16B shows plots of MIR-IR spectra of photoresist thin films on a CDO wafer for polymer quantification using isolated IR peaks in accordance with an embodiment of the invention.

As shown in FIGS. 15B and 16B, with proper selection of background spectra, MIR-IR can differentiate and quantify two different thicknesses of photoresist thin films by scaled absorbance subtraction with excellent spectra resolution. FIG. 15B shows the spectra of the photoresist thin film on the CDO on silicon wafer using Si(100) as the background spectra. FIG. 16B shows the spectra of the photoresist thin film on the CDO on silicon wafer using the combined CDO and Si(100) background spectra.

As shown in FIG. 15B, the CDO ILD only wafer exhibits mainly, as expected, an asymmetric —$CH_3$ stretching peak at 2970 $cm^{-1}$. Accordingly, the additional IR absorbance from 2925 to 2800 $cm^{-1}$ can be attributed to the organic polymers (to simulate post-etch residues). In addition, it can be seen that the C—H stretching peaks (3000-2800 $cm^{-1}$) and O—H stretching peaks (3700-3100 $cm^{-1}$) are useful to follow for decreasing quantities of photoresist on the CDO because as the photoresist is diluted and ultimately removed, the absorbance at the stretching peaks is reduced. As shown in FIG. 16B, the resulting IR integrated absorbance under the C—H stretching peaks (3000-2800 $cm^{-1}$) match well with the photoresist films of two decreasing thickness, 50× dilution vs. 300× dilution.

The excessive decreases of 2970 $cm^{-1}$ (—$CH_3$) and increase of 3400 $cm^{-1}$ (—OH) IR peaks can be used to evaluate the extent of CDO ILD damages after RIE and post-etch clean treatment. Oxygen plasmas will preferentially attack weaker Si—C bonds in porous CDO ILD and thus strip carbon, cause densification, and result in increased dielectric k values. In addition, carbon stripping by plasma processes also makes low-k CDO ILD's more prone to water damage during subsequent wet cleans processes. As illustrated by FIG. 17, the MIR-IR systems and methods of embodiments of the invention can sensitively detect the minute water adsorption on damaged CDO ILD base on the intense O—H stretching peak at >3200 $cm^{-1}$.

Example 3

Improvements to MIR-IR with Added Isotope Effect

The IR absorption peak locations (e.g., wave number, frequency, absorbance can be shifted by using different isotopes (such as $^{13}C$ and $^{18}O$) when performing plasma etching. The use of the isotopes enables additional improvements to characterization in certain embodiments employing the subject MIR-IR techniques. The IR absorption peak location shifts systematically according to the following equation for the stretching frequency (in reciprocal centimeters).

$$v = 1/2\pi c \sqrt{k/\mu},$$

where v gives the stretching frequency/wavenumber of absorbance, k is the spring constant for the chemical bond, c is the speed of light, and μ is the reduced mass of the A-B system.

The reduced mass of the A-B system can be given by:

$$\mu = m_A m_B / m_A + m_B,$$

where $m_i$ is the mass of atom i.

For example, replacing plasma etching gases (e.g., $CF_4$, $CH_2F_2$, CO) with $^{13}C$ enrichment, can shift the IR peak location to aid in identification and quantification of organic residues. The following illustrate some of the substitutions that are anticipated within this context:

$^{13}C$=O vs. $^{12}C$=O shift to lower frequency by about 40 $cm^{-1}$ $^{13}C$—H vs. $^{12}C$—H shift to lower frequency by about 9 $cm^{-1}$ $^{13}C$—F vs. $^{12}C$—F shift to lower frequency by about 33 $cm^{-1}$ $^{13}C$—Si vs. $^{12}C$—Si shift to lower frequency by about 22 $cm^{-1}$ Example 4

Fabrication of Waveguide (Preprocessing Step)

Figure 18A:
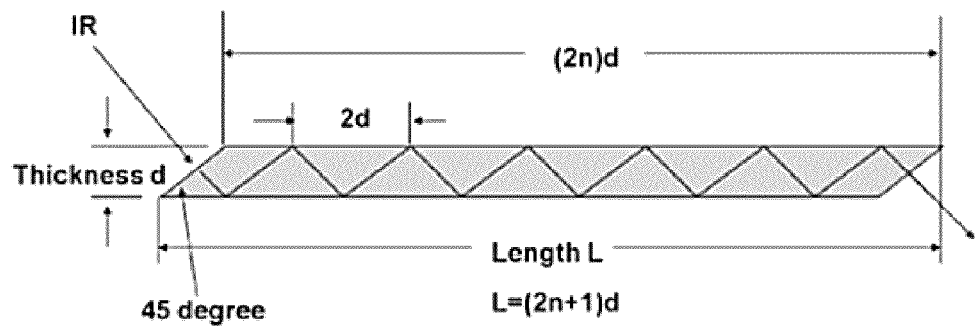
FIGS. 18A-18C show physical dimension features for fabricating IR waveguides in accordance with certain embodiments of the invention.
Figure 18B:
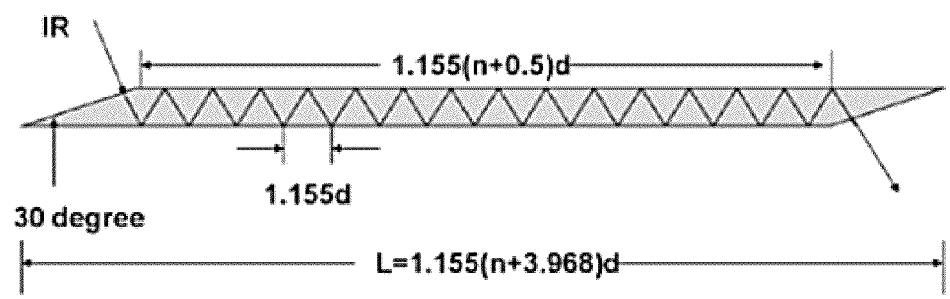
Figure 18C:
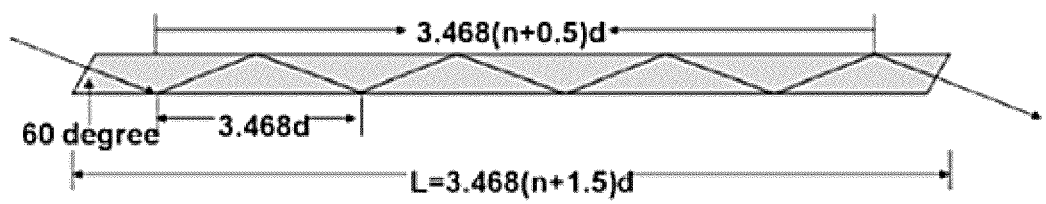

In accordance with one embodiment of the invention, a method of fabricating an IR waveguide is provided. The method includes cutting a patterned wafer into pieces having a suitable dimension. The wafers can include, but are not limited to Ge and Si substrates. As generally illustrated in FIGS. 18A-18C, physical dimensions of Si waveguides designed with bevel angles of 30, 45, and 60 degrees for MIR-IR as applied to various embodiments of the present invention are provided. The optimized length (Li) of waveguides can be calculated as Li=(2n+1)*d. For example, given a Si wafer with d=0.070 cm, L=5.665 cm (close to ideal length), and the two sides having 45 degree angles, the ideal length Li=(2*40+1)*0.070=5.67 cm (80 reflections). When the length is closer to (2n)*d, such as 5.6 cm or 5.74 cm, there is lower IR throughput. Tables 1 and 2 provide example dimensions suitable for certain embodiments of the invention (design examples for wafer thickness d=0.06 cm).

TABLE 1

| Polished angle | # of reflections | Ideal length | Fail length |
| --- | --- | --- | --- |
| 30 degree | 132 | 5.657 cm | 5.616 cm, 5.696 cm |
| 45 degree | 80 | 5.67 cm | 5.6 cm, 5.74 cm |
| 60 degree | 44 | 5.705 cm | 5.583 cm, 5.827 cm |

TABLE 2

| Polished angle | # of reflections | Ideal length | Avoid length |
| --- | --- | --- | --- |
| 30 degree | 132 (n = 66) | 4.849 cm (+0.069 cm) | 4.884 cm |
|  | 134 (n = 67) | 4.918 cm | 4.953 cm |
|  | 136 (n = 68) | 4.987 cm | 5.022 cm |
| 45 degree | 80 (n = 40) | 4.86 cm (+0.12 cm) | 4.92 cm |
|  | 82 (n = 41) | 4.98 cm | 5.04 cm |
|  | 84 (n = 42) | 5.10 cm | 5.12 cm |
| 60 degree | 44 (n = 22) | 4.890 cm (+0.208 cm) | 4.994 cm |
|  | 46 (n = 23) | 5.098 cm | 5.202 cm |
|  | 48 (n = 24) | 5.306 cm | 5.410 cm |

Figure 19A:
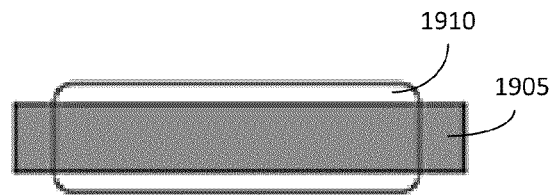
FIGS. 19A and 19B show a top down view and side view, respectively, of a wafer piece for fabricating an IR waveguide in accordance with an embodiment of the invention.
Figure 19B:
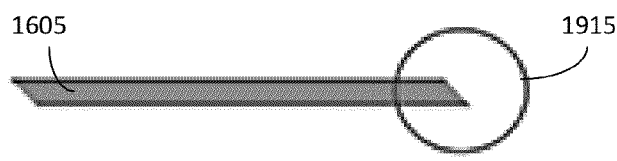

The cutting of the patterned wafer may be carried out in a clean room area (at least clean room 100) to protect the ULK ILD from contamination. Referring to the top down view of FIG. 19A and side view of FIG. 19B, the area 1910 of a wafer piece 1905 should be protected from contamination during the polishing process to form the angled beveled faces 1915.

Figure 20A:
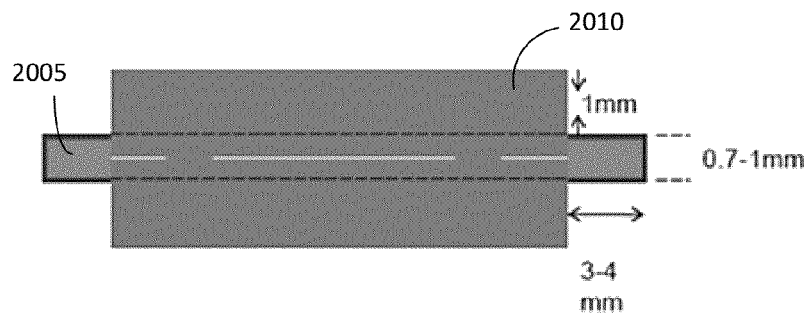
FIGS. 20A and 20B show a side view and end view, respectively, of a polishing enclosure case to protect a waveguide during fabricating of an IR waveguide in accordance with an embodiment of the invention.
Figure 20B:
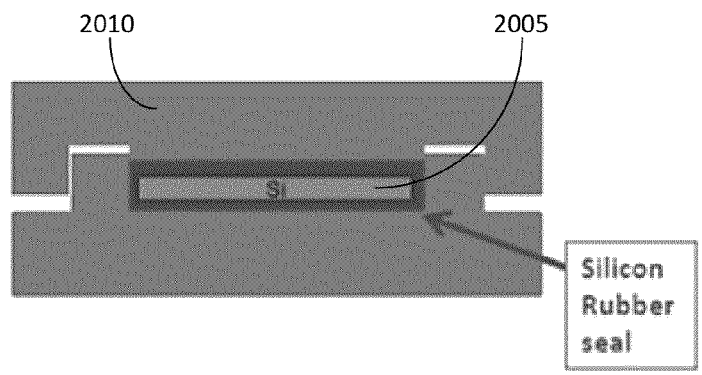
Figure 21:
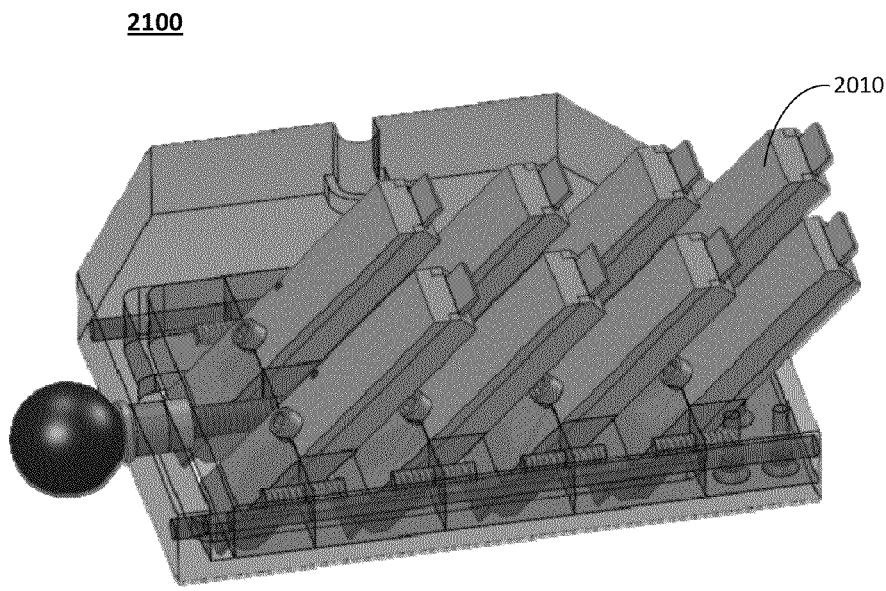
FIG. 21 shows an enclosure case holder for a polishing system for fabricating IR waveguides in accordance with an embodiment of the invention.

Once the wafer is cut into the pieces, the wafer pieces (e.g., Si wafer piece 2005) can be inserted into a protective waveguide enclosure case 2010 as shown in the side-view of FIG. 20A and the end view of FIG. 20B. The protective waveguide enclosure case 2010 can be loaded into a case holder 2100 such as shown in FIG. 21, for polishing by an automated polisher with micron polishing resolution control. The optically smooth bevel faces can be prepared using increasing finer polishing steps followed by optical microscope inspection to ensure optical smooth finishing. One suitable automated polisher is the MultiPrep™ polishing system from Allied High Tech.

To minimize the contaminated area and labor involved in fabricating the waveguide with a common rotating polishing platen, automatic numerical machining can be used to prepare Si and Ge waveguides. A rotating polishing head can be controlled by numerical machining to cut and polish preset bevel faces for IR waveguide.

Once the beveled faces are formed in the waveguides, the Si or Ge waveguides are removed from the polishing system and the protective waveguide enclosure case 2010. The waveguides may undergo an organic cleaning process. Any contaminated ULK dielectric layer can etched away using 5% (by weight) HF, if needed. The completed IR waveguide preprocessing presents a wafer ready for MIR-IR measurements.

Example 5

MIR-IR Test Set-Up

Rectangular waveguides and square waveguides can be fabricated for ex-situ MIR-IR measurement by, for example, following a method as described in Example 4. For certain of the experiments carried out as described with respect to Examples 1 and 2, an ex-situ measurement system was built.

Figure 22A:
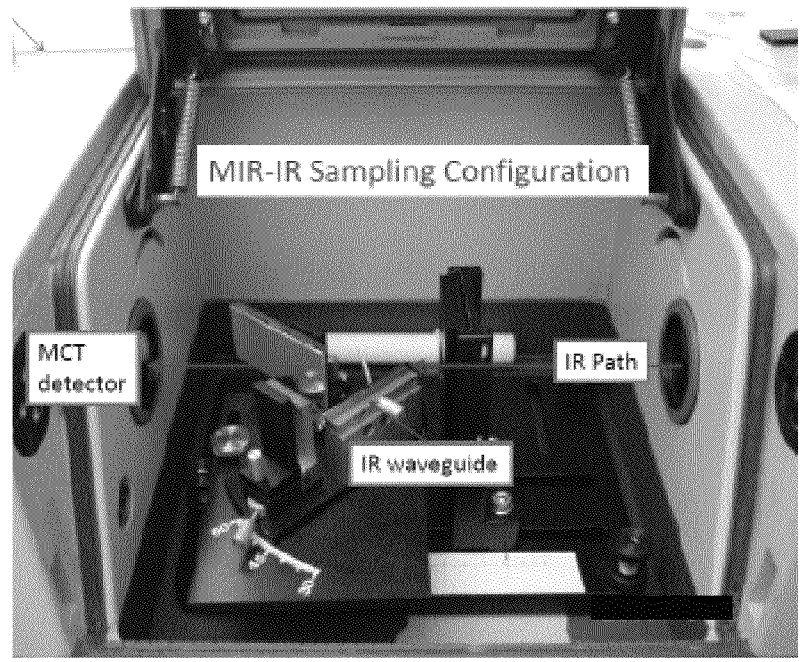
FIGS. 22A-22D are annotated photographs of MIR-IR sample chamber system configurations in accordance with example embodiments of the invention.
Figure 22B:
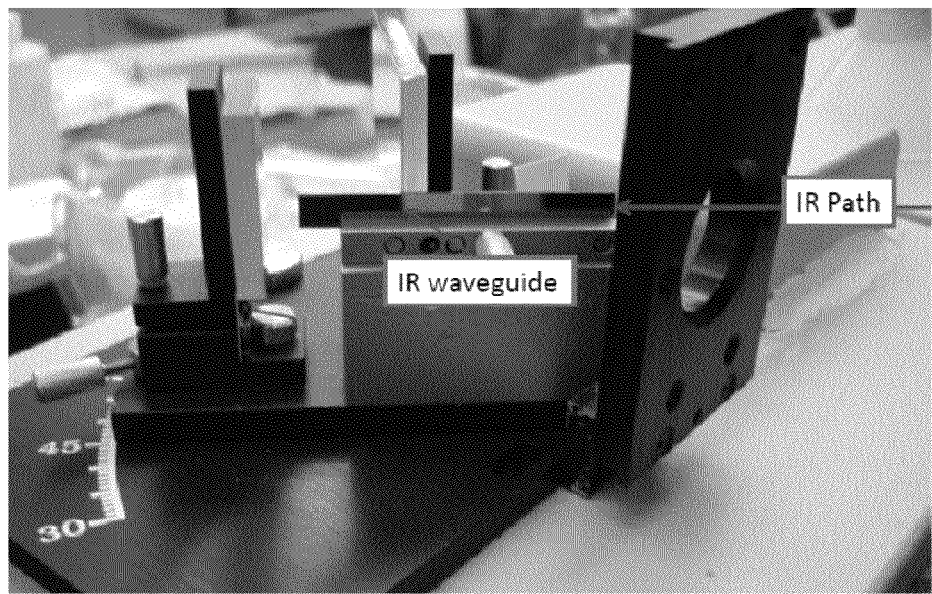
Figure 22C:
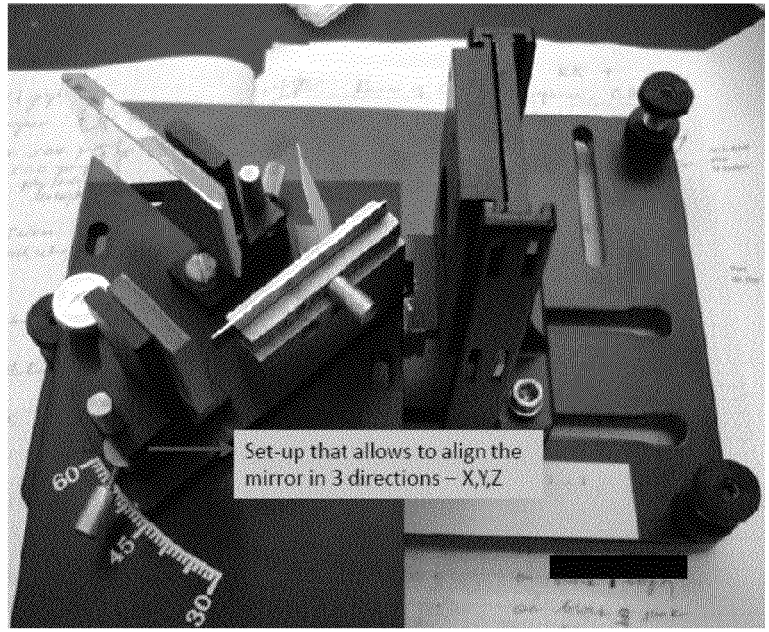

FIGS. 22A-22D show annotated photographs of the MIR-IR sample chamber used for MIR-IR measurements. According to certain embodiments, a polished IR waveguide is placed in a variable angle Attenuated Total Reflection (ATR) accessory, such as shown in FIG. 22B. The ATR accessory can be placed in the sampling chamber of a FTIR spectrometer, as shown in FIG. 22A. By fine tuning the adjustment of mirror positions of the ATR accessory (see FIG. 22C), the IR signal passing through the IR waveguide can be maximized and detected by the MCT detector in the FTIR spectrometer (see FIG. 22A) and highly sensitive MIR-IR spectrum can thus be obtained.

Figure 22D:
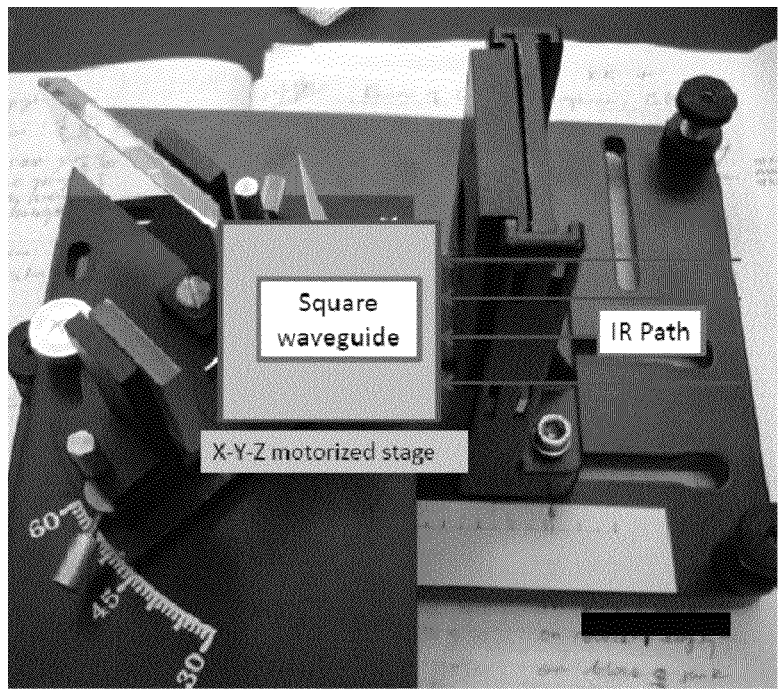

FIG. 22D illustrates the equipment setup utilized for ex-situ MIR-IR measurements of square waveguides (e.g., one inch square) within some embodiments of the invention. Because the bevel face of the IR waveguide is longer than in the rectangular waveguide configuration, multiple MIR-IR sampling can be performed.

Multiple sampling can be performed by either scanning the IR incident beam or multiple IR incident beams or moving square waveguides with a X-Y-Z motorized stage driven by precision liner stepping motors.

In accordance with various aspects of the invention, one or more of the following may be achieved by certain embodiments of the invention: monitoring plasma reactive ion etching (RIE) of low k (and ULK) dielectric trench features on silicon, germanium, SiGe, and other wafer technologies; detecting trace post-etch polymer residue; detecting trace post-etch cleaning residue; providing an ex-situ monitoring tool; providing an in-situ monitoring tool; and assisting photoresist formulation and process development. In addition, the MIR-IR of various, non-limiting embodiments of the invention is applied utilizing IR waveguides (internal reflection elements) directly from patterned wafers; and used in conjunction with spectra analysis tools to provide for sensitive detection of post-etch residues. According to certain embodiments, MIR-IR is applied in a batch wafer processing environment by fabricating bevel faces at the edges of a monitor wafer; and is applied in a batch wafer processing environment by fabricating bevel faces at the bottom face of a wafer.

It should be understood that the above listing is not intended to be exhausting or to be limiting for each embodiment disclosed herein. These features may be achieved in part or in whole by one or more of the disclosed inventions.

Any reference in this specification to "one embodiment," "an embodiment," "example embodiment," etc., means that a particular feature, structure, or characteristic described in connection with the embodiment is included in at least one embodiment of the invention. The appearances of such phrases in various places in the specification are not necessarily all referring to the same embodiment. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

It should be understood that the examples and embodiments described herein are for illustrative purposes only and that various modifications or changes in light thereof will be suggested to persons skilled in the art and are to be included within the spirit and purview of this application.

What is claimed is:

1. A method of characterizing a patterned wafer, comprising:
    receiving a wafer having undergone a semiconductor fabrication patterning process, the wafer comprising a waveguide;
  performing multiple-internal reflection (MIR)-infrared (IR) spectroscopy by irradiating a first angled surface of the wafer using an IR source to achieve internal reflection within the waveguide of the wafer and detecting IR transmission/absorption in the waveguide from radiation exiting a second angled surface of the wafer using an IR detector;
    processing a signal received by the IR detector in a computer system to provide an absorbance spectra; and
    analyzing the absorbance spectra to provide a characterization of material on the wafer having undergone the semiconductor fabrication process.

2. The method according to claim 1, wherein the semiconductor fabrication patterning process comprises depositing a dielectric film on the wafer,
the absorbance spectra comprising the absorbance spectra of the dielectric film.

3. The method according to claim 1, wherein the semiconductor fabrication patterning process comprises performing at least one of depositing a photoresist on the wafer, baking the photoresist on the wafer, photo-exposure of the photoresist on the wafer, developing the photoresist on the wafer, etching/removing the photoresist on the wafer, and post-etching/post-removal of polymer residues of the photoresist on the wafer,
    the absorbance spectra comprising the absorbance spectra of the photoresist.

4. The method according to claim 3, wherein depositing the photoresist on the wafer comprises depositing the photoresist on a dielectric film on the wafer.

5. The method according to claim 4, wherein the semiconductor fabrication patterning process further comprises performing a plasma reactive ion etching of the dielectric film.

6. The method according to claim 1, wherein analyzing the absorbance spectra to provide the characterization of material on the wafer having undergone the semiconductor fabrication patterning process comprises identifying and quantifying polymer residues on a dielectric film by integrated IR peak absorbance and/or scaled absorbance subtraction, the dielectric film being a dielectric film deposited on the wafer.

7. The method according to claim 1, wherein the waveguide of the wafer is formed before the wafer undergoes the semiconductor fabrication patterning process.

8. The method according to claim 1, further comprising forming the waveguide of the wafer by forming the first angled surface and the second angled surface at opposing sides of the wafer.

9. The method according to claim 8, wherein forming the first angled surface and the second angled surface comprises performing a polishing process to side edges of the wafer to create a 30 to 60 degree angle.

10. The method according to claim 1, further comprising forming the waveguide of the wafer by forming the first angled surface and the second angled surface at a back face of the wafer by etching the back face of the wafer.

11. The method according to claim 1, wherein analyzing the absorbance spectra to provide the characterization of material on the wafer having undergone the semiconductor fabrication patterning process comprises comparing absorbance spectra to a background absorbance spectra to perform scaled absorbance subtraction and/or integrated IR peak absorbance using chemical bonding IR peak locations.

12. The method according to claim 1, wherein analyzing the absorbance spectra to provide the characterization of material on the wafer having undergone the semiconductor fabrication patterning process comprises identifying chemical structures using chemical bonding IR peak locations.

* * * * *